United States Patent
Khanicheh et al.

(10) Patent No.: US 10,524,639 B2
(45) Date of Patent: Jan. 7, 2020

(54) MEDICAL DEVICE STAND

(71) Applicant: HOYA Corporation, Tokyo (JP)

(72) Inventors: Azadeh Khanicheh, Somerville, MA (US); Isaac Ostrovsky, Wellesley, MA (US); Michael Barenboym, Boston, MA (US); Hrishikesh Vishvas Deo, Brooklyn, NY (US)

(73) Assignee: HOYA Corporation, Tokyo (JP)

( * ) Notice: Subject to any disclaimer, the term of this patent is extended or adjusted under 35 U.S.C. 154(b) by 481 days.

(21) Appl. No.: 14/810,019

(22) Filed: Jul. 27, 2015

(65) Prior Publication Data

US 2017/0027422 A1    Feb. 2, 2017

(51) Int. Cl.
| | |
|---|---|
| *A47F 5/00* | (2006.01) |
| *A61B 1/00* | (2006.01) |
| *A61B 17/00* | (2006.01) |

(52) U.S. Cl.
CPC .............. *A61B 1/00149* (2013.01); *A61B 2017/00292* (2013.01); *A61B 2017/00991* (2013.01)

(58) Field of Classification Search
CPC ..... A61B 1/00149; A61B 50/20; A61B 50/22; A61B 50/26; F16M 11/046
USPC ....................................... 248/125.8
See application file for complete search history.

(56) References Cited

U.S. PATENT DOCUMENTS

| | | | | |
|---|---|---|---|---|
| 4,854,301 A | * | 8/1989 | Nakajima | A61B 1/00147 600/102 |
| 5,613,305 A | * | 3/1997 | Narrin | A45D 20/12 34/90 |
| 6,248,101 B1 | * | 6/2001 | Whitmore, III | A61B 1/00149 606/1 |
| 2008/0154089 A1 | | 6/2008 | Kanazawa | |
| 2008/0188868 A1 | | 8/2008 | Weitzner et al. | |

FOREIGN PATENT DOCUMENTS

JP        2004-275203 A    10/2004

OTHER PUBLICATIONS

PCT Notification of Transmittal of the International Search Report and the Written Opinion of the International Searching Authority issued in International Application No. PCT/IB2016/000936, dated Oct. 26, 2016.

* cited by examiner

*Primary Examiner* — Todd M Epps
(74) *Attorney, Agent, or Firm* — Finnegan, Henderson, Farabow, Garrett & Dunner, LLP

(57) ABSTRACT

Embodiments of the disclosure may include an endoscope floor stand. In accordance with one embodiment, an endoscope floor stand may include a base and an adjustable body. The body may include at least a first elongated structure having a first end and a second end, wherein the first end is connected to the base. The body may also include at least a second elongated structure slideably moveable relative to the first elongated structure to adjust a height of the endoscope floor stand, and the second elongated structure may be suspended above the base. The stand may also include a ball joint, wherein at least a portion of the ball joint is configured to removably couple to an end of the body located opposite the base. The ball joint may also include a holder extending from the ball joint and dimensioned to receive an endoscope.

29 Claims, 31 Drawing Sheets

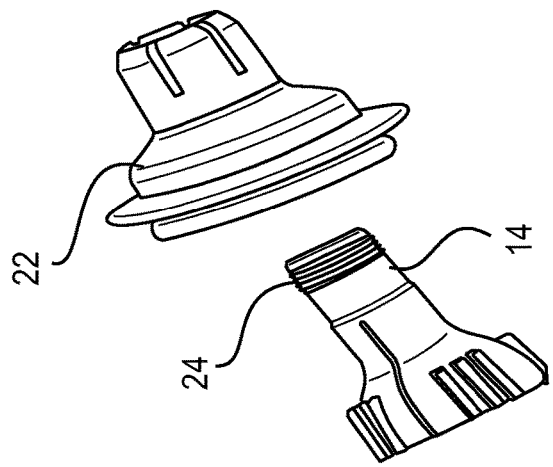
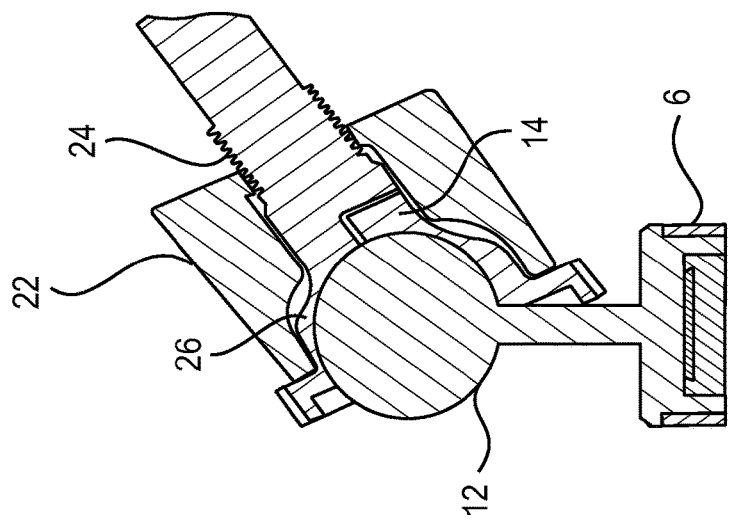
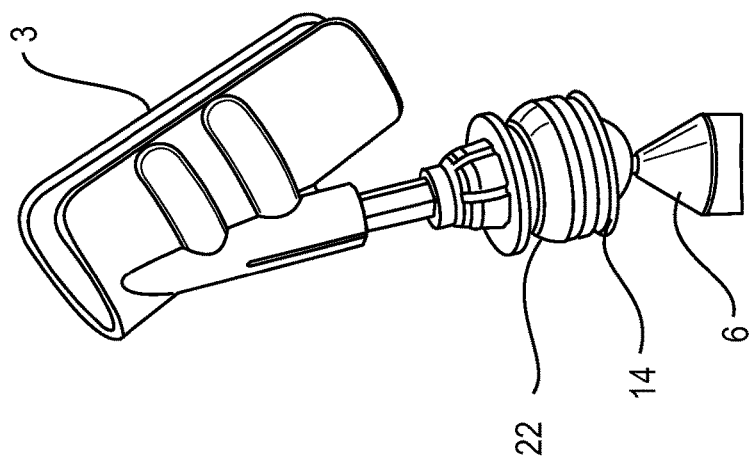
FIG. 8C
FIG. 8B
FIG. 8A

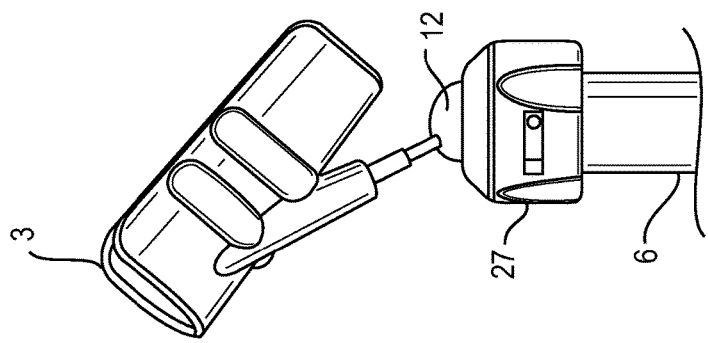
FIG. 10E
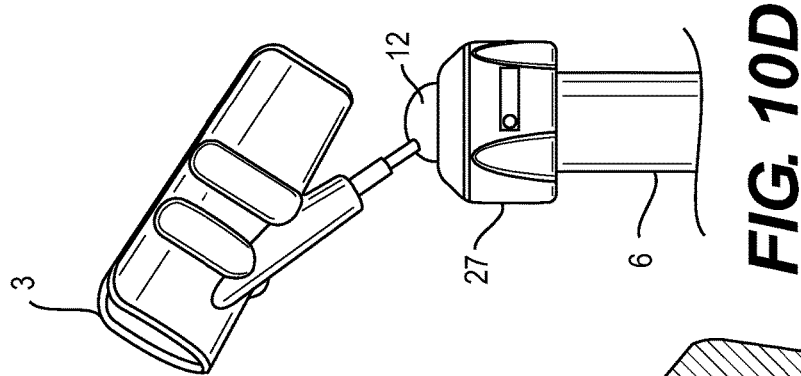
FIG. 10D
FIG. 10F
FIG. 10C
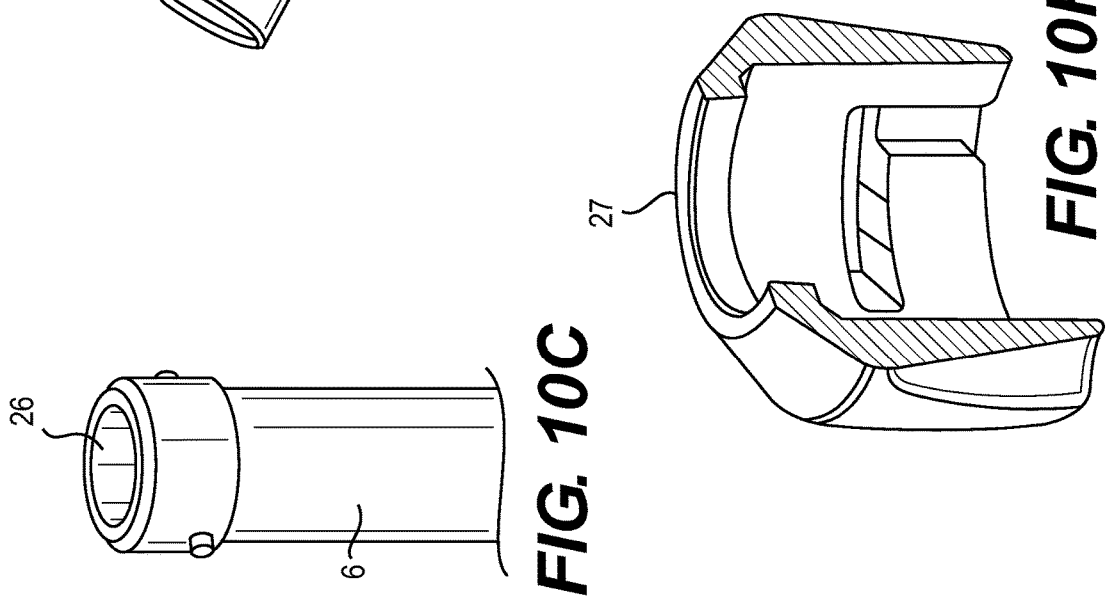

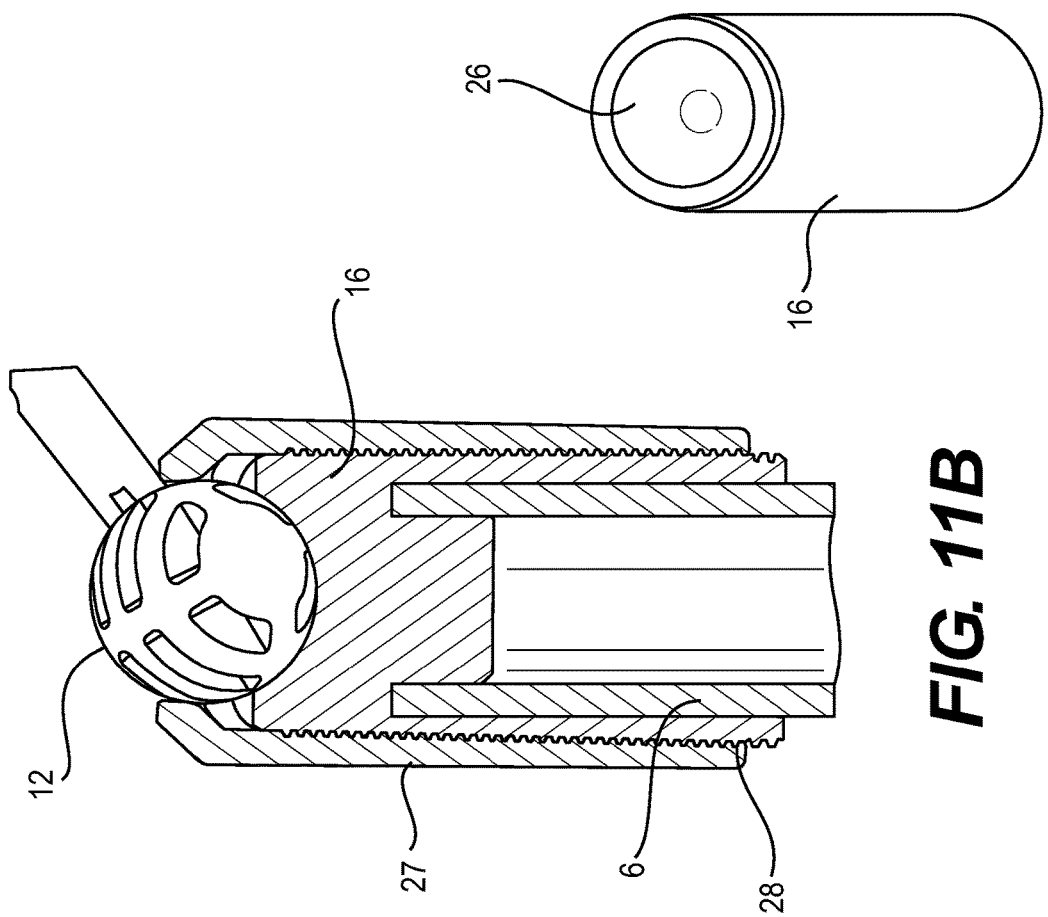
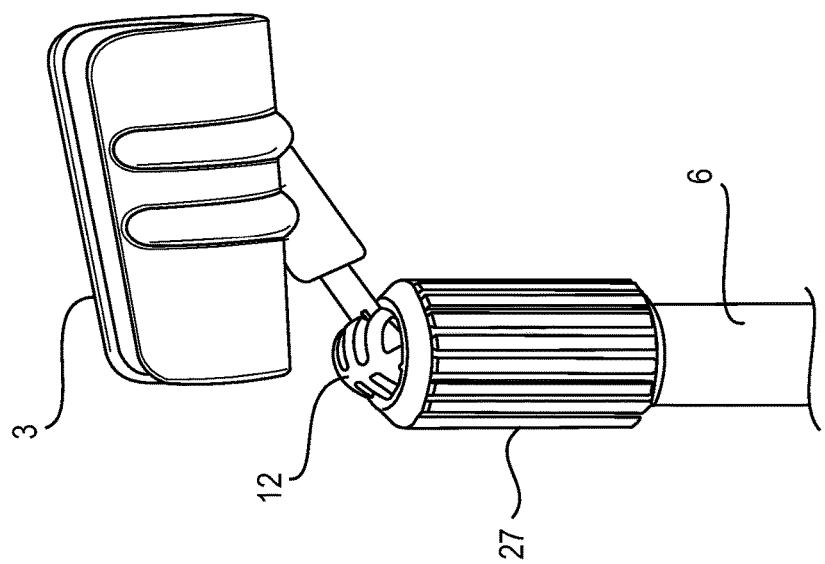
FIG. 11B
FIG. 11A

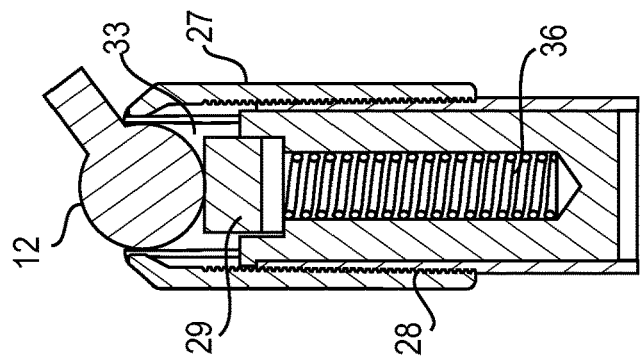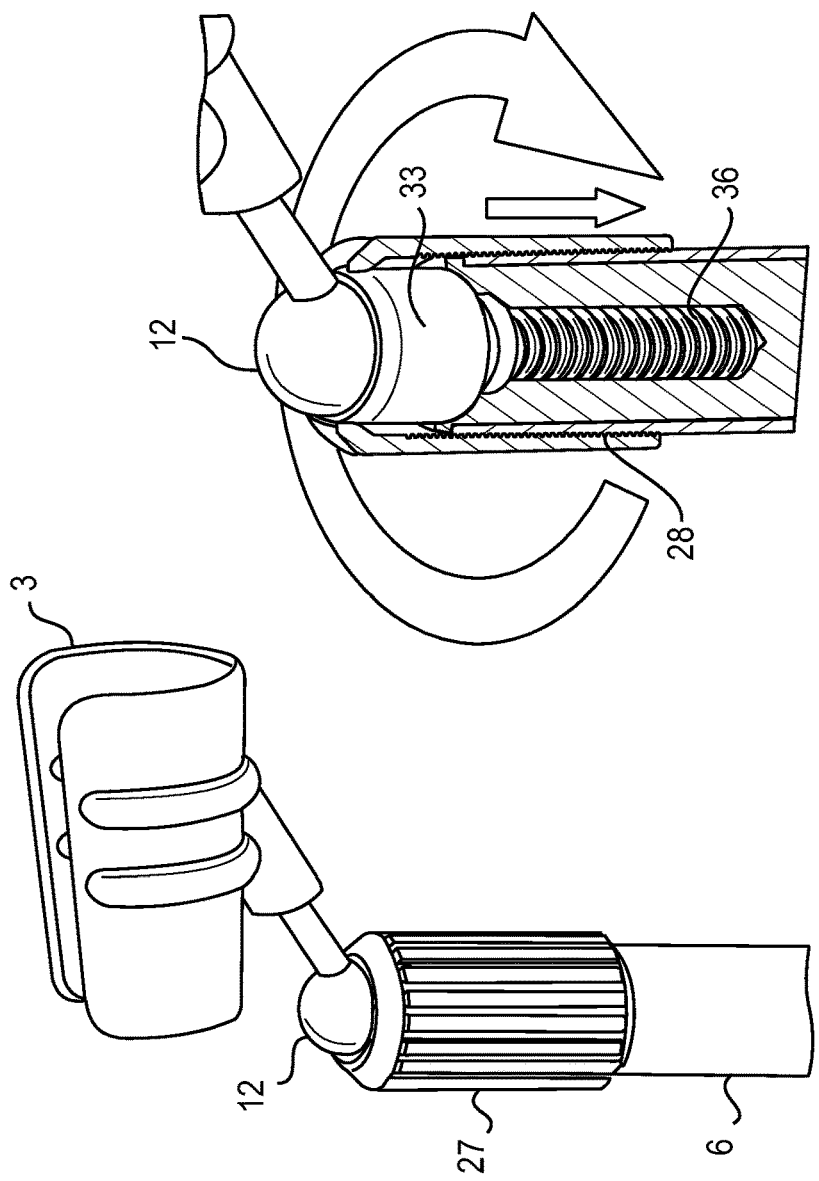
FIG. 12C
FIG. 12B
FIG. 12A

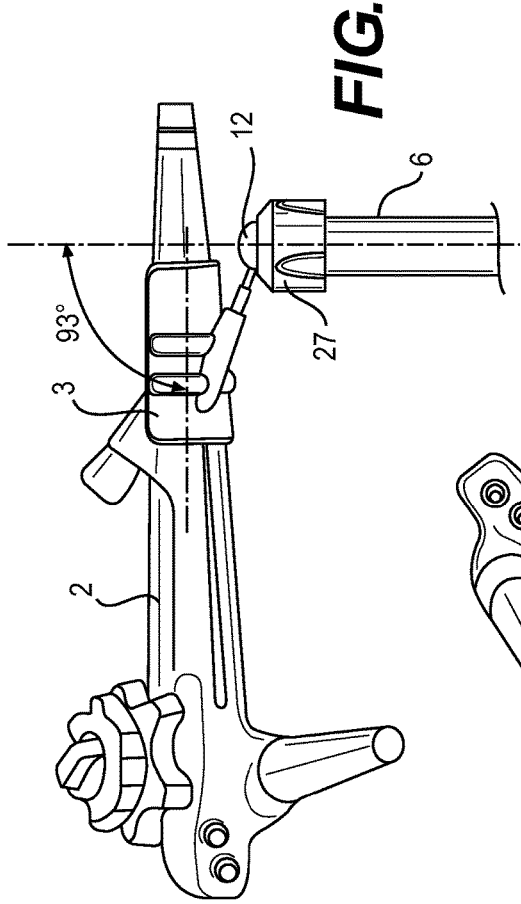
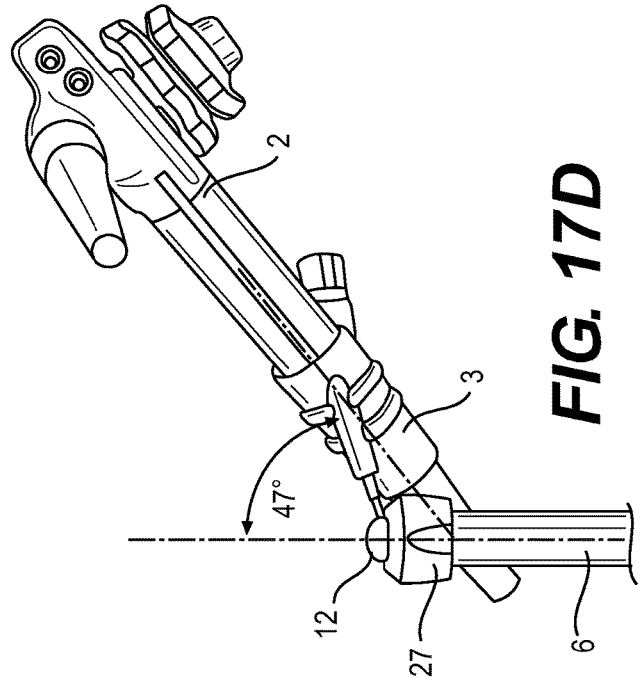
FIG. 17C
FIG. 17D

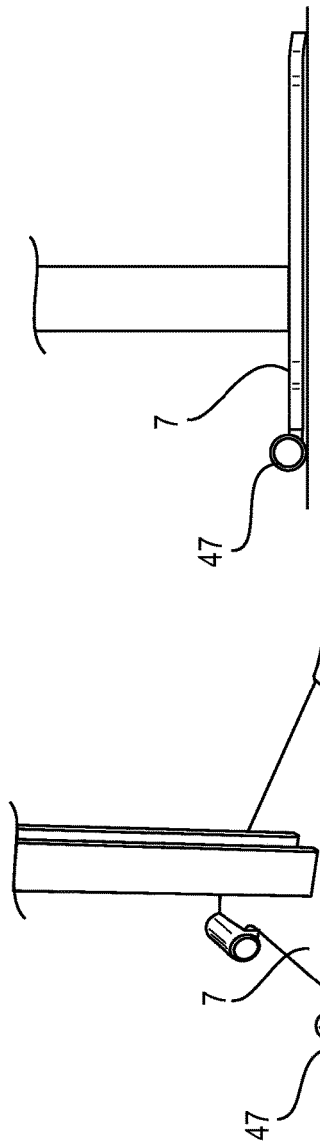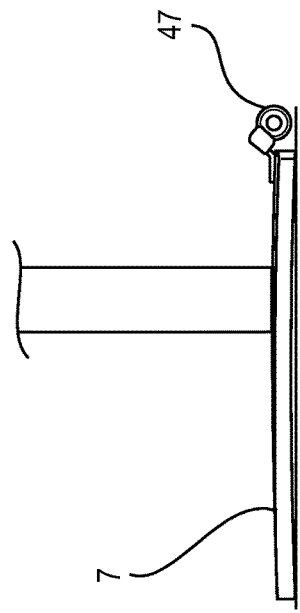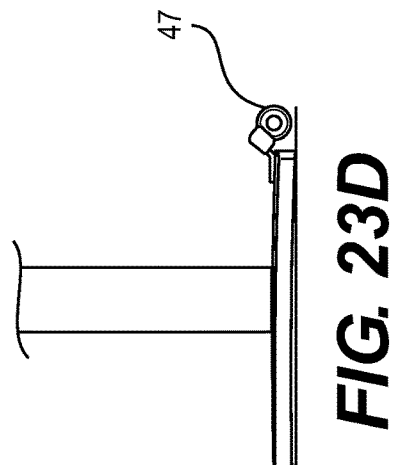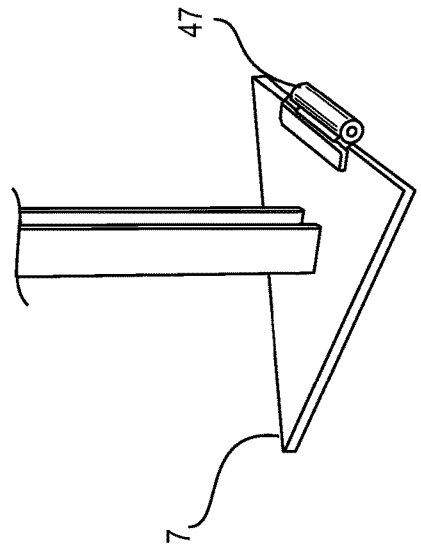

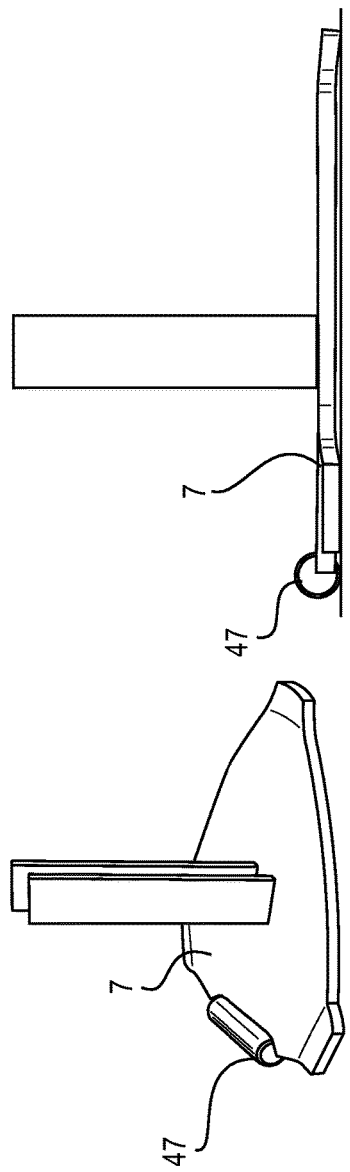
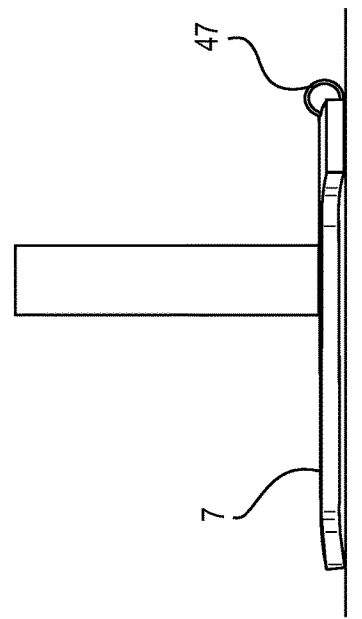
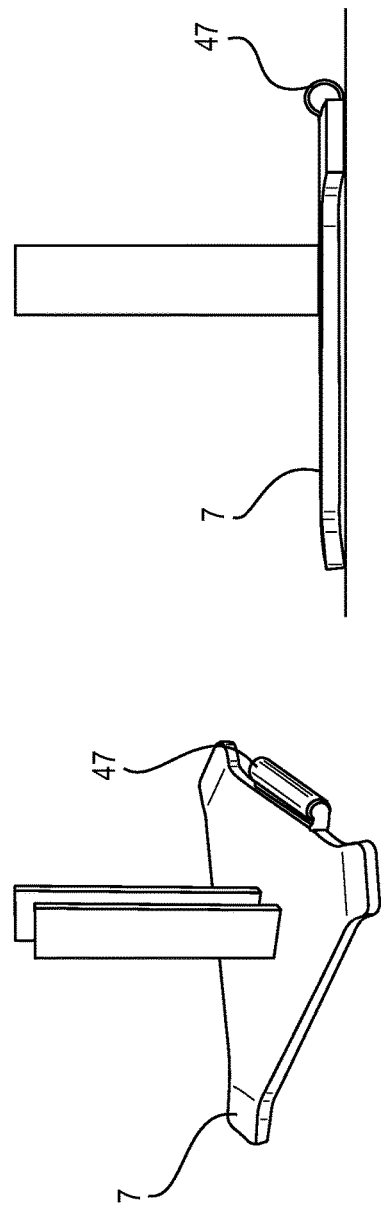

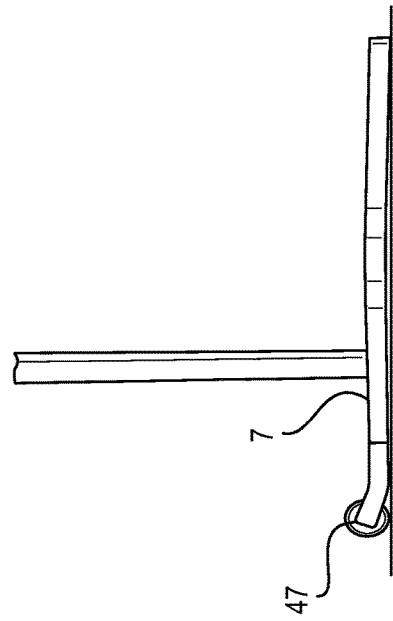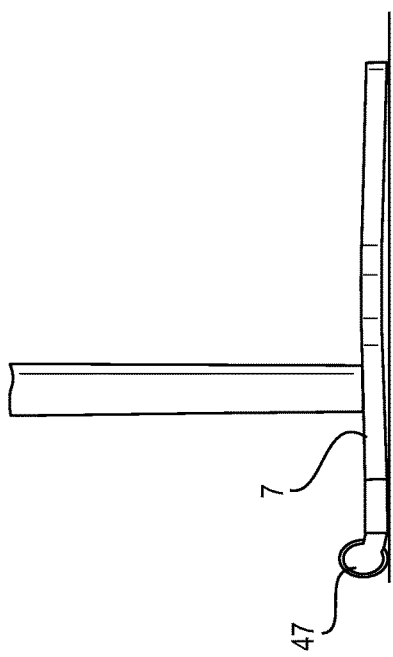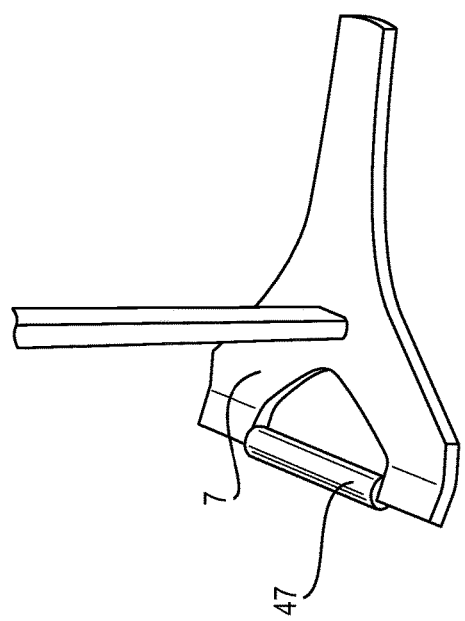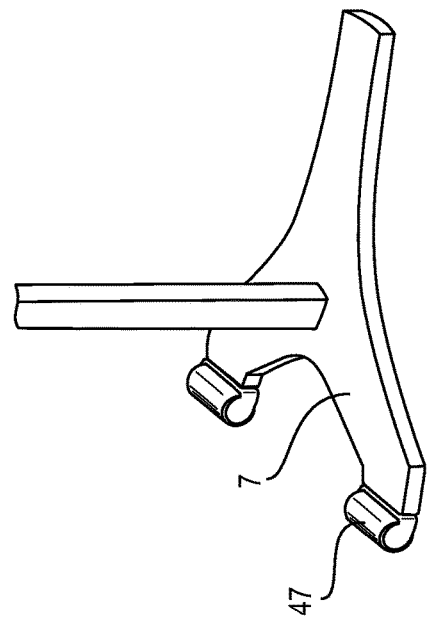

MEDICAL DEVICE STAND

TECHNICAL FIELD

Embodiments of the present disclosure relate to stands for supporting medical devices, and more particularly, to stands for supporting endoscopic instruments during use.

BACKGROUND INFORMATION

Minimally invasive procedures have grown in popularity, and more physicians are utilizing endoscopic procedures to perform biopsies, surgeries, and other procedures, to make diagnoses, or to visualize an area of concern located within a patient's body. By allowing the physician to gain access to internal target areas using natural orifices and/or small incision sites, endoscopic procedures may reduce trauma to the patient, and the patient may experience quicker recovery times, less residual scarring, or fewer side effects.

The increasing use of endoscopes has had consequences for physicians, however. Endoscopes are often bulky or heavy and can be unwieldy to hold and manipulate. The elongate insertion tube designed to be inserted into the patient and the umbilical cord of the endoscope that connects the endoscope to a light source and/or fluid source can be heavy and awkward to balance, support, and control. To manipulate an endoscope, knobs and buttons may need to be repeatedly engaged by a physician's hand, while the other hand may need to move the scope's insertion tube in and out of the body or rotate the tube in various directions to maneuver the distal end to a site within the body and/or to perform a procedure. In addition to the endoscope itself, physicians often need to manipulate tools extending through the endoscope during a procedure. As a result physicians may need to support and manipulate a scope in awkward and uncomfortable positions for long periods of time. And in some instances, endoscopic surgeries may take more time to perform than traditional, open-body surgeries.

Over time physicians that regularly use endoscopes may experience more aches and pains in their hands, wrists, arms, back, or upper body due to the unnatural and repetitive nature of holding and manipulating an endoscope. Physicians may experience carpel tunnel, lateral epicondylitis (tennis elbow), arthritis, or other painful or potentially debilitating problems as a result of endoscope use. Additionally, smaller physicians or physicians with smaller hands may have difficulty holding and manipulating endoscopes.

While attempts have been made to increase the ergonomics of endoscopes, many of these new ergonomic devices have not caught on. Physicians learn to perform procedures on traditional endoscopes, and many do not use devices that would change the way that they interact with the scope, because they would need to re-learn how to perform the procedures using the new device. Using new devices may require changes to the techniques that physicians have always used and may require them to alter years of learned muscle memory. They are often concerned about how long it will take to "reprogram" their movements and way of thinking to adjust to something new. Even simply changing the way a physician holds an endoscope may affect the tactile feedback that a physician is accustomed to or may make the physician less comfortable when controlling the endoscope. As a result, physicians often opt for traditional, less-ergonomic devices, because that is what they are used to.

Thus, there exists a need for an improved device that would make an endoscope more ergonomic for a physician to use. A device is needed that would reduce injuries to physicians caused by repetitive motions and overuse when manipulating the buttons, knobs, and other actuators of an endoscope. A device is also needed to improve access to endoscope actuators and provide easier tool and accessory manipulation, including for those physicians having smaller hands. There is further need for a device that is capable of supporting the weight of an endoscope without significantly impeding the physician's manipulation, rotation, and movement of the endoscope in multiple degrees of freedom. Additionally, the device should be able to be used with a range of different endoscope types, shapes, and/or sizes, should not significantly affect the physician's interaction with the scope, and should be easily cleaned and/or sterilized between uses and quick and easy to set up. Embodiments of the present disclosure seek to address one or more of these problems.

SUMMARY

Embodiments of the present disclosure are directed to a stand for use with an endoscope. Various embodiments of the disclosure may include one or more of the following aspects.

In accordance with one embodiment, an endoscope floor stand may include a base and an adjustable body. The body may include at least a first elongated structure having a first end and a second end, wherein the first end is connected to the base. The body may also include at least a second elongated structure slideably moveable relative to the first elongated structure to adjust a height of the endoscope floor stand, and the second elongated structure may be suspended above the base. The stand may also include a ball joint, wherein at least a portion of the ball joint is configured to removably couple to an end of the body located opposite the base. The ball joint may also include a holder extending from the ball joint and dimensioned to receive an endoscope.

Various embodiments of the endoscope stand may include one or more of the following features: the ball joint may be fully pre-assembled, and the entire ball joint may be removably coupled to the end of the body; the ball joint may be included as part of the holder, and the ball joint and holder may removably couple to the end of the body; a ball of the ball joint may be included as part of the holder; a ball of the ball joint may be included as part of the body; the portion of the ball joint configured to removably couple to the end of the body may include a recess configured to receive the ball of the ball joint; the end of the body located opposite the base may include a recess for receiving a ball of the ball joint; a resistance to movement of the ball joint may be adjustable; the holder may move relative to a ball of the ball joint and independent from the ball of the ball joint; a resistance of the holder to movement may be different than a resistance of the ball to movement; the ball joint may be configured to allow the holder to move relative to the body within a first range of 0-180 degrees in a first plane; within a second range of 0-180 degrees in a second plane, and within a third range of 0-360 degrees in a third plane; the ball joint may be configured to allow the holder to rotate relative to the body; the body may not include telescoping portions or the body may include at least one telescoping portion; the body may be formed of an inner tube slideably disposed within an outer tube, and the outer tube may not wrap completely around a perimeter of the inner tube so that a portion of the inner tube is exposed when disposed within the outer tube; and the body may include a third elongated structure having a first end and a second end, wherein the first end of the third elongated structure is connected to the base, and wherein the second elongated structure is suspended above the base between the first elongated structure and the third elongated structure.

In some embodiments, an endoscope floor stand may include a weighted base and a body having an adjustable height. The body may be formed of at least a first elongated structure extending up from the base and having a first end coupled to the base and a second end, an adjustment mechanism located at a region of the second end of the first elongated structure, and at least a second elongated structure moveably coupled to the adjustment mechanism, wherein the adjustment mechanism and the second elongated structure cooperatively make the height of the body adjustable. The stand may also include a ball joint, wherein at least a portion of the ball joint is configured to removably couple to the body at a region opposite the base, and a holder coupled to the ball joint and configured to receive an endoscope, wherein the ball joint is configured to allow the holder to move relative to the body in at least three degrees of freedom.

Various embodiments of the endoscope stand may include one or more of the following features: the holder may be rotatable; a ball of the ball joint may be located on an end of the body opposite the base; the ball joint may be formed of the ball and an adapter, the adapter may have a recess configured to receive at least a portion of the ball, the adapter may be removably coupled to the ball, and the adapter may include a fastening mechanism configured to tighten the adapter around the ball; the adapter may be included as part of the holder; the holder may be configured to rotate relative to the ball joint; a resistance of the holder to movement may be different than a resistance of the ball joint to movement; the ball joint may include a ball and at least one of a locking nut or a locking adapter; and the body may include a recess located on an end of the body opposite the base and the recess may be configured to receive the ball.

Embodiments of the disclosure also include a device for coupling to a body of an endoscope stand and for holding an endoscope during use. The device may include a ball joint, wherein at least a portion of the ball joint is configured to removably couple to the body of the endoscope stand. The device may also include a holder coupled to the ball joint and configured to receive an endoscope. The ball joint may allow the holder to move in at least three degrees of freedom.

In various embodiments, the holder may be moveably coupled to the ball joint; the holder may be rotatable; the ball joint may also include an adapter configured to removeably couple to the body of the endoscope stand, and a fastening mechanism configured to compress the adapter to couple the device to the body of the endoscope stand; the ball joint may include a ball and at least one of a locking nut and a locking adapter; and the device may include a separate connector configured to couple to the body of the endoscope stand, and the ball joint may be configured to couple with the connector in order to couple the ball joint and the holder to the body of the endoscope stand.

In some embodiments, a device for coupling to a body of an endoscope stand and for holding an endoscope during use may include an adapter having a recess configured to receive a rounded portion of the body of the endoscope stand to cooperatively form a ball joint. The adapter may be configured to removably couple the device to the rounded portion of the endoscope stand. The device may further include a fastening mechanism configured to compress the adapter to couple the device to the body of the endoscope stand and a holder coupled to the adapter and configured to receive an endoscope. The holder may be moveable around the rounded portion of the endoscope stand in at least three degrees of freedom when coupled to the body of the endoscope stand.

In various embodiments of the device, the holder may be rotatably coupled to the adapter; the holder may be removably coupled to the adapter; and the device may also include at least one of a locking nut, a locking adapter, a buckle, or a screw mechanism for tightening the adapter.

Additional objects and advantages of the embodiments will be set forth in part in the description that follows, and in part will be obvious from the description, or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings:

FIG. 8A depicts an exemplary joint, according to an embodiment of the present disclosure;

FIG. 8B depicts a cross-sectional view of the joint of FIG. 8A, according to an embodiment of the present disclosure;

FIG. 8C depicts an exploded view of two components of the joint of FIG. 8A, according to an embodiment of the present disclosure;

FIG. 10O-10F depict components of an exemplary joint, according to an embodiment of the present disclosure;

FIG. 11A depicts an exemplary joint, according to an embodiment of the present disclosure;

FIG. 11B depicts a cross-sectional view of the joint of FIG. 11A, according to an embodiment of the present disclosure;

FIG. 12A depicts an exemplary joint, according to an embodiment of the present disclosure;

FIG. 12B depicts a partial, cross-sectional view of the joint of FIG. 12A, according to an embodiment of the present disclosure;

FIG. 12C depicts a cross-sectional view of the joint of FIG. 12A, according to an embodiment of the present disclosure;

FIGS. 17C and 17D depict exemplary ranges of motion of a stand, according to an embodiment of the present disclosure;

FIGS. 23A-23L depict bases of exemplary stands, according to embodiments of the present disclosure.

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts. For purposes of this disclosure, an "endoscope" may refer to any suitable type of scope for insertion into a patient during a medical procedure. Endoscopes may include, for example, colonoscopes, duodenoscopes, gastroscopes, sigmoidoscopes, enteroscopes, ureteroscopes, and bronchoscopes. The term "procedure" broadly refers to the insertion of an endoscope into a patient for any purpose, including, but not limited to, surgery, biopsy, diagnosis, treatment, visualization, implantation of a device, suction, or insufflation. The term "elongated structure" generally refers to a hollow, solid, or hollowed out half-structure (e.g., a pole, rod, dowel, post, bar, etc.) of any shape (e.g., circular, square, rectangular, triangular, flattened, etc.) having a length longer than a width and extending between two ends.

While the present disclosure is described herein with reference to illustrative embodiments of stands used for particular applications, such as for performing medical procedures, it should be understood that the embodiments described herein are not limited thereto. For example, scopes and similar devices are often used in industrial applications, e.g., to inspect and/or repair machinery. Stands of the present disclosure may also be used with industrial scopes in non-medical settings. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

Figure 1:
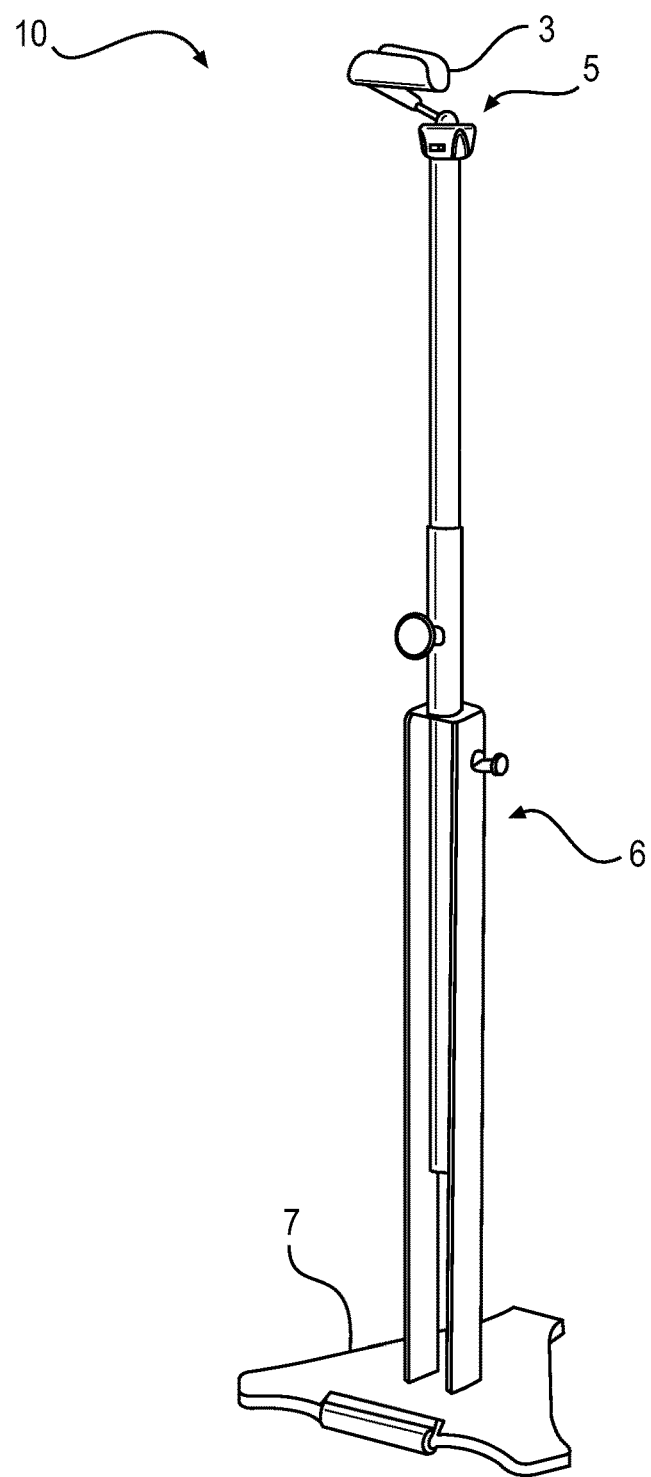
FIG. 1 illustrates an exemplary endoscope stand, according to an embodiment of the present disclosure.
Figure 2:
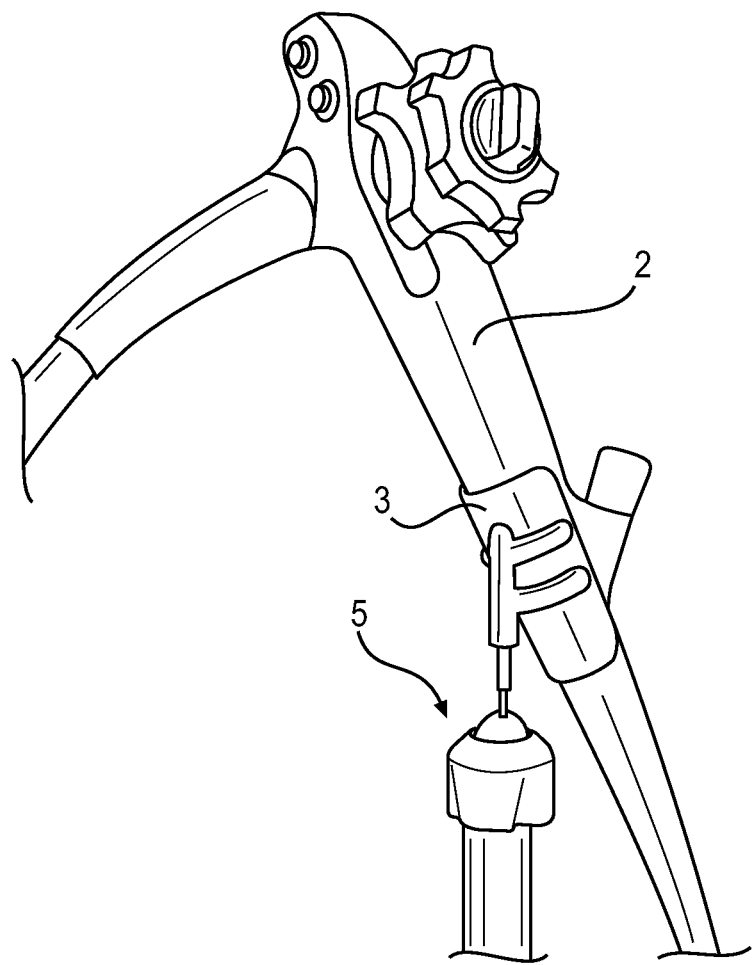
FIG. 2 depicts an endoscope supported by an exemplary stand; according to an embodiment of the present disclosure.

Prior to providing a detailed description, the following overview generally describes the contemplated embodiments. As is shown in FIGS. 1 and 2, exemplary stands 10 of the present disclosure may hold and support endoscopes 2 during use by a physician. Stands 10 support the weight of the endoscope instead of the physician and may act as an extra hand. Stand 10 may include several main components, such as a holder 3 for engaging endoscope 2 and holding endoscope 2 on stand 10, a joint 5 for allowing the physician to move endoscope 2 while mounted on stand 10, a body 6 for supporting the endoscope, and a base 7. Holder 3 may be configured to allow a user to easily but securely mount and unmount different types or models of endoscope 2 on stand 10. For example, holder 3 may slideably receive endoscope 2 within it, or endoscope 2 may friction- or snap-fit within holder 3. To securely mount endoscope 2, holder 3 may have a shape that is complimentary to, or is the negative of, the portion of endoscope 2 that holder 3 is configured to engage. In some embodiments, holder 3 may be biased inwards or may include a material, texture (e.g., grooves or ridges), coating, or other suitable surface configuration to allow holder 3 to more securely grip endoscope 2 within it.

Joint 5 may be configured to allow the user to freely move endoscope 2 in multiple degrees of freedom and to rotate endoscope 2. Once a user lets go of endoscope 2, joint 5 may be configured to keep holder 3 and endoscope 2 in place so that the endoscope stays positioned where the user last moved it. The user can then freely reposition the endoscope as necessary during the procedure, each time the endoscope will remain in the position in which it was last left. In some embodiments, the user may also be able to lock stand 10 after a user lets go of endoscope 2 so that endoscope 2 cannot be further moved unless stand 10 is unlocked. This may allow a physician to hold endoscope 2 in place during a procedure once a desired location in the patient has been reached, even if endoscope 2 or stand 10 are bumped during the procedure.

Body 6 may be adjustable in height to allow stand 10 to accommodate physicians of different heights or to accommodate physicians whether standing or sitting. Base 7 may be shaped and weighted to securely support the endoscope when moved in different directions and angles to inhibit tipping of the stand. Additionally, the overall footprint of stand 10 may be shaped and dimensioned so as to not trip up or get in the way of a physician during use and to facilitate cleaning between procedures. These components, among others, their interactions, and overall use of the stand are described in further detail below.

Figure 3A:
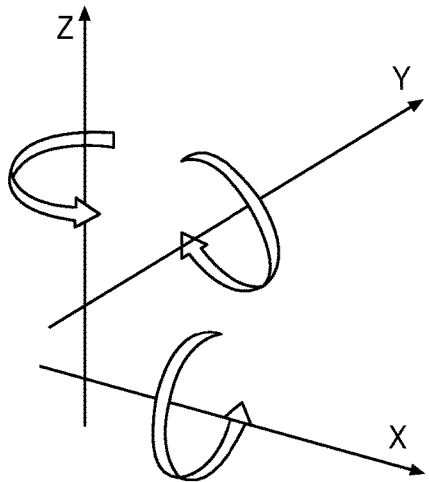
FIGS. 3A-3C illustrate exemplary ranges of movement of an endoscope stand, according to embodiments of the present disclosure.

When a physician holds an endoscope during a procedure, the physician has the ability to move and adjust the endoscope freely in virtually any direction by flexing a wrist or arm or using other body movements. As is shown by the arrows in FIG. 3A, joint 5 of stand 10 may be configured to allow for rotational movements, side-to-side movements, back-to-front rocking movements, or off-axis rocking movements. Joint 5 provides for motion in three planes (xy, xz, yz). In some embodiments, the range of motion may be, for example, 0-180 degrees in the y-z and x-z planes (although in some embodiments, ranges of greater than 180 degrees may be used) and 0-360 degrees in the x-y plane.

Figure 3B:
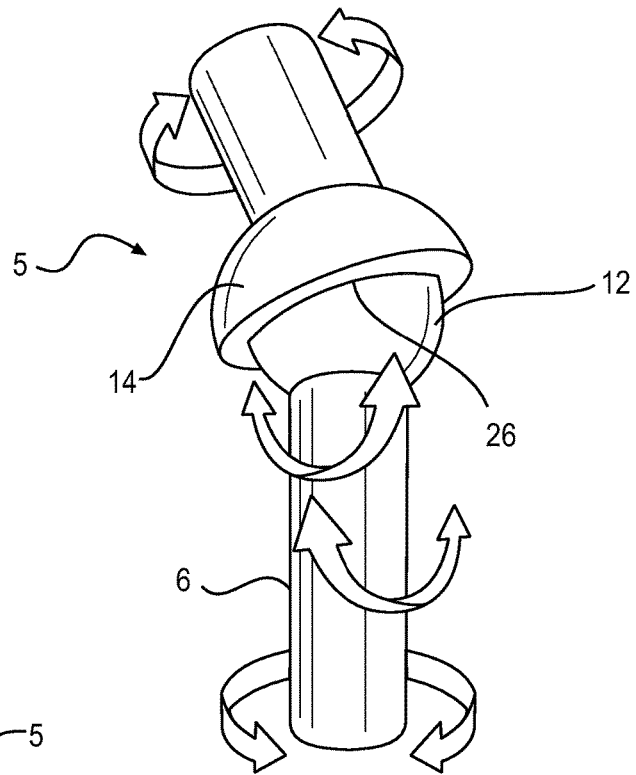
Figure 3C:
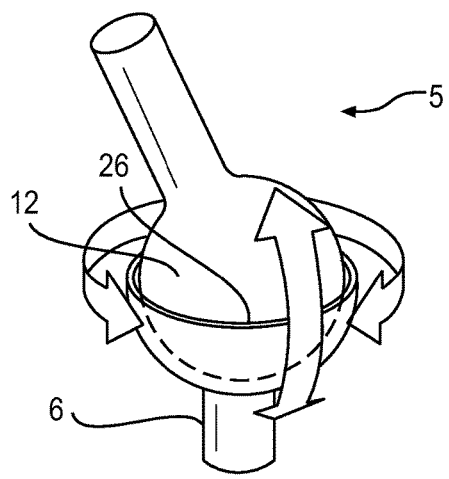

As is shown in FIGS. 3B and 3C, the interaction of a ball 12 and a recess 26 in joint 5 may provide for this range of motion. Recess 26 or ball 12 may move or rotate relative to the other. In the embodiment of FIG. 3B, ball 12 remains in place on body 6, while recess 26 of adapter 14 receives ball 12 and allows adapter 14 to move around ball 12. Exemplary embodiments depicting the configuration of FIG. 3B include those discussed in reference to FIG. 5 through FIGS. 9A-9DE. In the embodiment of FIG. 3C, the configuration is reversed. Recess 26 is incorporated as part of body 6, and ball 12 moves within recess 26 to provide the desired range of motion. Exemplary embodiments depicting the configuration of FIG. 3C include those discussed in reference to FIGS. 10A-10F through FIGS. 11A-11B.

In the various exemplary embodiments, holder 3 may also be configured to rotate around an axis independently from the movement of ball 12. For example, holder 3 may rotate around an axis along which holder 3 is connected to ball 12, e.g., around an axis of groove 25, discussed further in regards to FIGS. 9A-9E. Joint 5 may enable this additional rotational movement by allowing rotation of a shaft that couples holder 3 to ball 12 or rotation of holder 3 relative to the shaft. In some embodiments, additional rotation independent of ball 12 may be enabled by rotation of joint 5 as a unit relative to an upper portion of body 6, or by rotation of an upper portion of body 6 to which joint 5 is connected. Free rotation of 360 degrees may be provided, or rotation may be more limited due to the specific configurations of one or more components of joint 5.

Figure 4C:
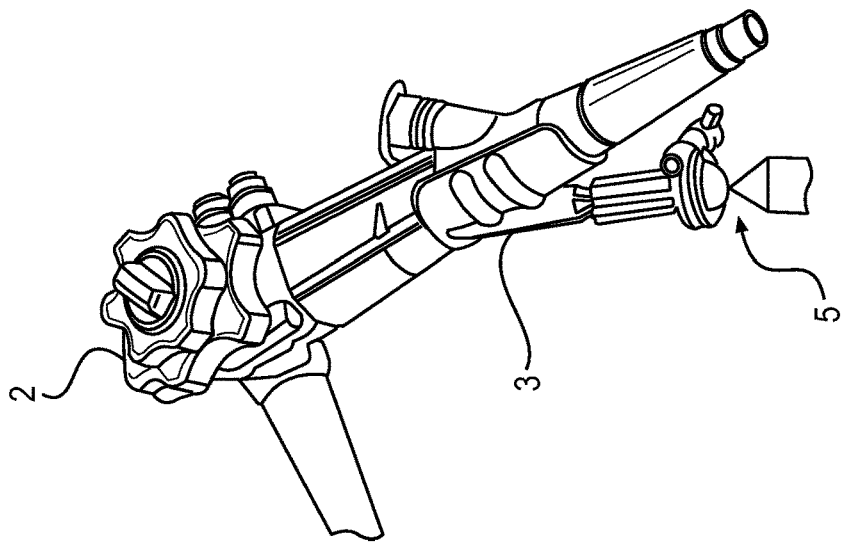
FIGS. 4A-4E depict exemplary ranges of movement of an endoscope when attached to a stand, according to embodiments of the present disclosure.
Figure 4B:
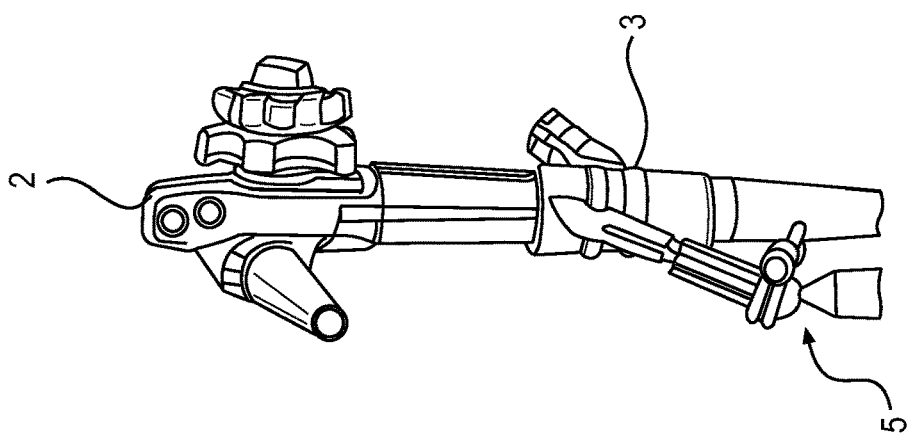
Figure 4A:
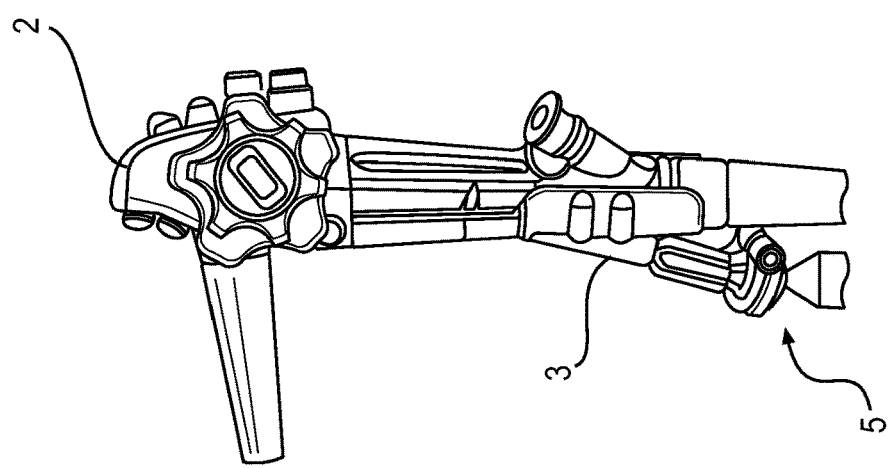
Figure 4D:
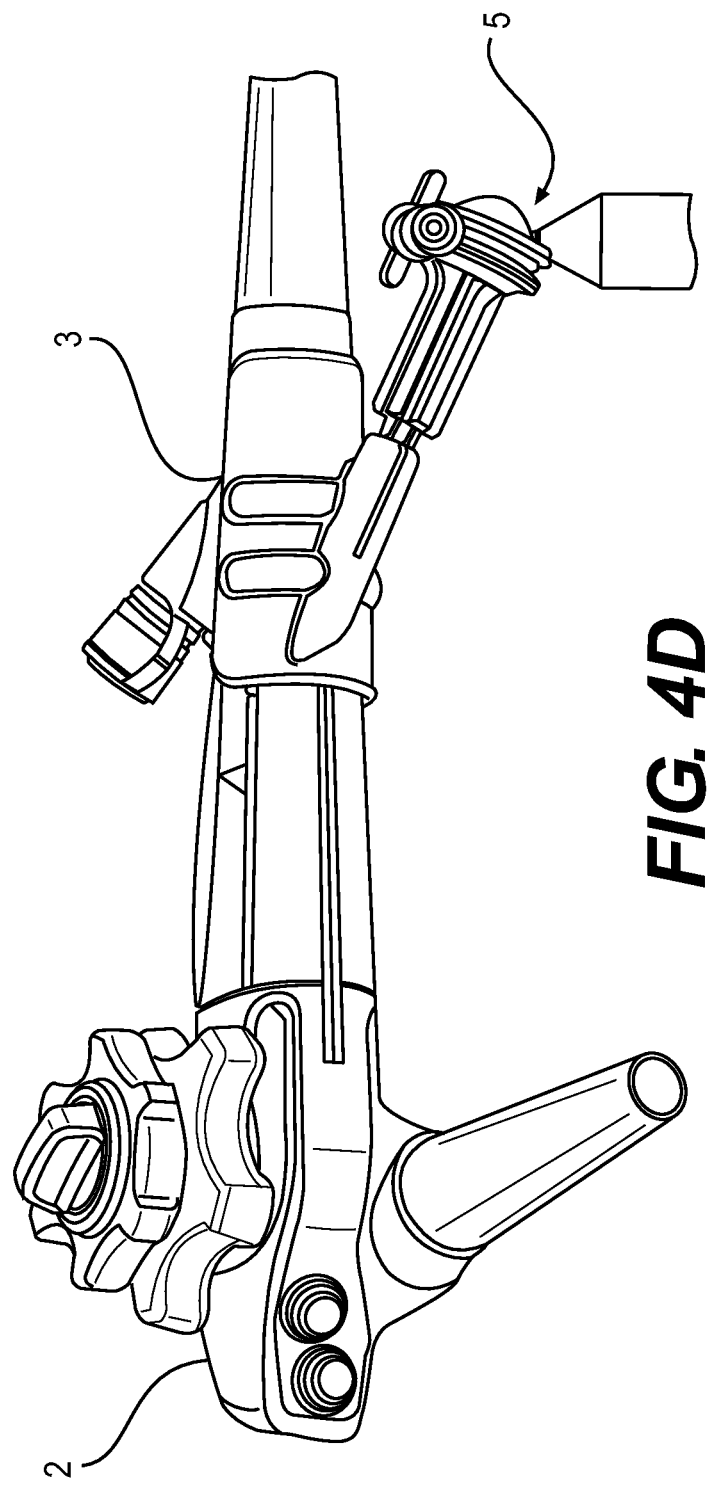
Figure 4E:
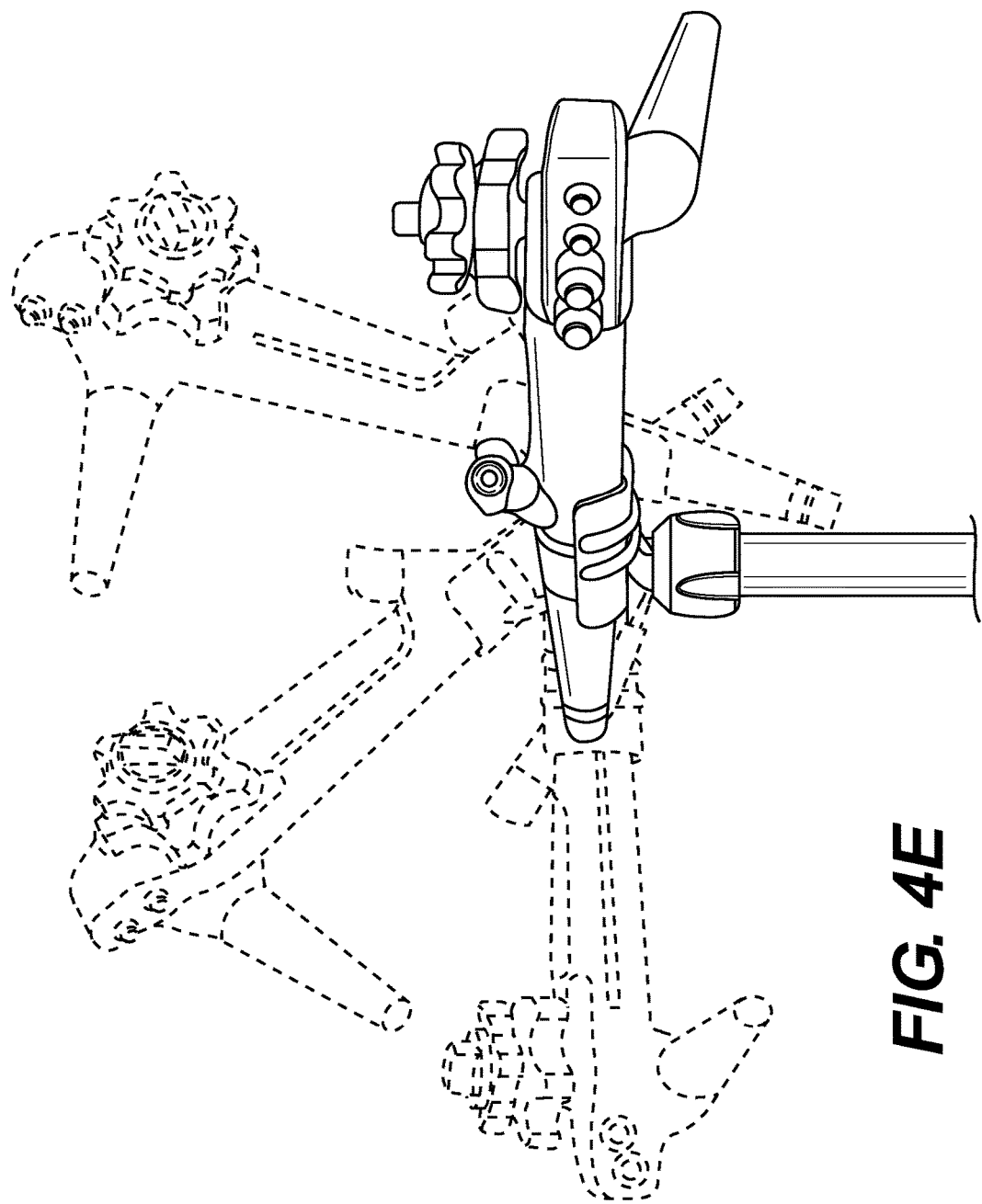
Figure 6:
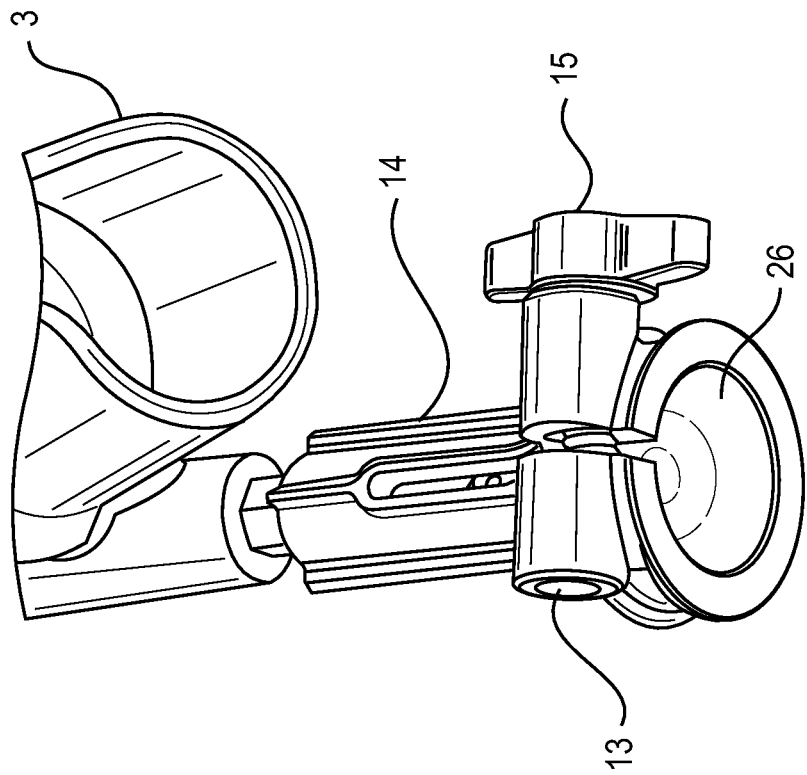
FIG. 6 illustrates additional optional components of the joint of FIG. 5, according to an embodiment of the present disclosure.

FIGS. 4A-4E depict an exemplary range of endoscope positioning that stand 10 may be configured to accommodate. Stand 10 may be able to hold endoscope 2 in a vertical or off-axis position, as is shown in FIGS. 4A-4C, or may hold endoscope 2 in a horizontal position, as is shown in FIG. 4D, or at any suitable angle in between. FIG. 4E depicts an exemplary range of motion of approximately 180 degrees along the x-z plane. In some embodiments, stand 10 may also allow a user to adjust the range of motion in one or more directions or axes. Accordingly, in order to meet the needs of physicians, exemplary embodiments of stand 10 may be designed to allow a user to adjust the positioning of endoscope 2 and holder 3 on stand 10 in a number of ways.

Physicians traditionally experience free range of motion when holding and operating an endoscope, and they do not experience high levels of resistance when achieving that motion. As mentioned above, maneuvering an endoscope may entail only flexing a wrist or using other smaller muscle groups. Accordingly, exemplary embodiments of stand 10 may be configured to offer little or virtually no resistance to movement of endoscope 2 on stand 10 by a user. Optionally, in some embodiments, resistance may be increased. Some embodiments may also be designed to allow a physician to increase or decrease the resistance as desired, for example, depending on the type of endoscope used, type of procedure being performed, stage of the procedure, or preference of the particular physician.

Although physicians may desire the ability to move an endoscope freely during a procedure, they may also not want endoscope 2 to fall out of position when mounted on stand 10 once they let go of the endoscope. In order to support the weight of endoscope 2 during a procedure, instead of the physician, holder 3 and/or joint 5 may be configured to substantially stay in place once a user lets go of the endoscope. Different embodiments of stand 10 may balance the ability to freely move endoscope 2 when mounted on stand 10 with the ability to substantially retain endoscope 2 in position once the physician stops moving endoscope 2. Different embodiments may achieve one or more of these goals in different ways, as discussed in detail below.

Figure 19:
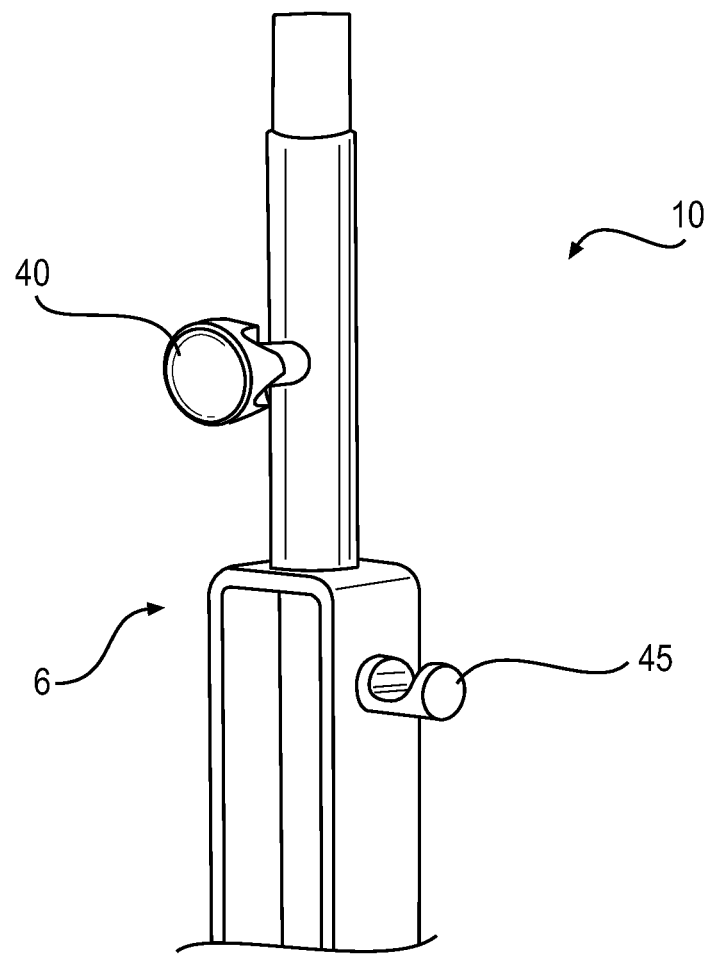
FIG. 19 illustrates an adjustable portion of an exemplary stand, according to an embodiment of the present disclosure.

Further, stand 10 may lock in position automatically once the physician stops moving endoscope 2 and may remain in place until the physician moves the endoscope again. In some embodiments, a user may be able to lock the endoscope in position manually, too, for example, so that the endoscope does not move unless unlocked, which may provide the ability to keep the endoscope in place during use when manipulating tools passing through the endoscope, visualizing a specific region of the patient, performing a resection or other procedure, etc. In some embodiments, stand 10 may include one or more hooks 45 or projections for holding, wrapping, or looping the endoscope insertion tube or light guide on during use, as is also shown in FIG. 19, discussed further below.

As will also be discussed below in further detail, various configurations of joint 5 and stand 10 are contemplated, and different elements of stand 10 may be permanently attached to one another, or elements of stand 10 may be removably attached to one another, e.g., to facilitate cleaning and/or sterilization. For example, holder 3 and all or part of joint 5 may be removably coupled to body 6. This may allow holder 3 and joint 5 to fit into an autoclave or similar machine to facilitate sterilization between use. Or, holder 3 and/or joint 5 may be disposable while body 6 and base 7 are reusable. Bulkier body 6 and base 7 may be swabbed down between uses while the smaller—and potentially harder to clean—mechanisms of holder 3 and/or joint 5 may be disposed of and replaced.

As is shown in FIGS. 3B and 3C, joint 5 is a ball joint around which endoscope 2 can move when mounted. In various embodiments, ball 12 of joint 5 may be included as part of body 6 (FIG. 3B), may be included as part of holder 3, or may be separate from body 6 and holder 3. In embodiments in which ball 12 is part of body 6 or holder 3, all of joint 5 may be completely preassembled as part of either body 6 or holder 3, or joint 5 may be split between body 6 and holder 3. The design of joint 5 may allow different portions of stand 10 to attach and release from one another, as described further below.

Figure 5:
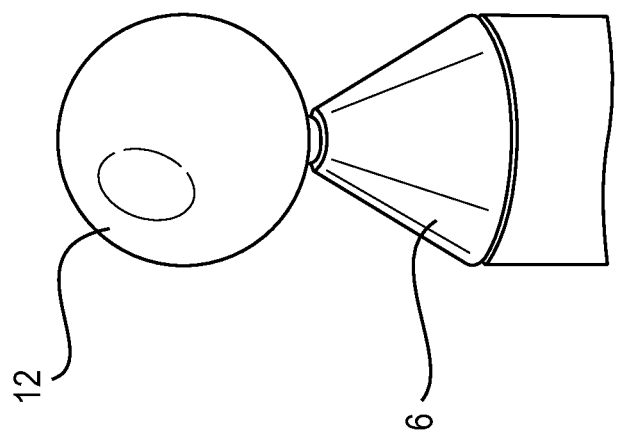
FIG. 5 depicts an exemplary joint, according to an embodiment of the present disclosure.

As shown in FIG. 5, ball 12 may be formed as part of body 6. In the embodiment shown in FIG. 6, holder 3 may include an adapter 14 configured to fit over ball 12. Adapter 14 includes a recess 26 that is sized and shaped to receive a portion of ball 12 either loosely or securely (e.g., friction- or snap-fit) within it. Once ball 12 is received within recess 26, and adapter 14 is positioned on ball 12, recess 26 may be tightened around ball 12 to fasten holder 3 in place. For example, in the embodiment of FIG. 6, adapter 14 includes and a screw mechanism 13 configured to attach holder 3 to ball 12. Adapter 14 may include a slit or opening in recess 26. Once placed on ball 12, a wingnut 15 of screw mechanism 13 may be turned to pull both sides of the opening towards each other, clamping adapter 14 onto ball 12 to create an interference fit between ball 12 and adapter 14. Wingnut 15 should be tightened enough to allow adapter 14 and holder 3 to be able to hold endoscope 2 in place and to provide free range of motion, but not so tight that the smoothness of adapter 14 moving around ball 12 is inhibited.

Alternatively, instead of including openings or slits, adapter 14 or a wall of recess 26 may be deformable or compressible to achieve compression of adapter 14 around ball 12 when tightened.

In some embodiments, the number of times wingnut 15 is rotated may affect the resistance of adapter 14 around ball 12 to movement. For example, stand 10 may include one or more visual, audible, or tactile indicators that may convey to a user the amount of resistance achieved by screwing or unscrewing wingnut 15 in order to adjust the resistance of stand 10. Exemplary indicators may include increased resistance to tightening, clicks, markings on a portion of stand 10 (e.g., a gauge or ruler or marking indicating that when wingnut 15 is tightened to that position, a certain level of resistance is achieved), rings or markings on ball 12, or other suitable indicators. In some embodiments, the indicators may be staggered in a series to convey to the user when various levels of resistance has been achieved. Accordingly, a user may be able to adjust the resistance of stand 10 by screwing or unscrewing wingnut 15, e.g., while setting up for a procedure, during a procedure, or between procedures.

Figure 7B:
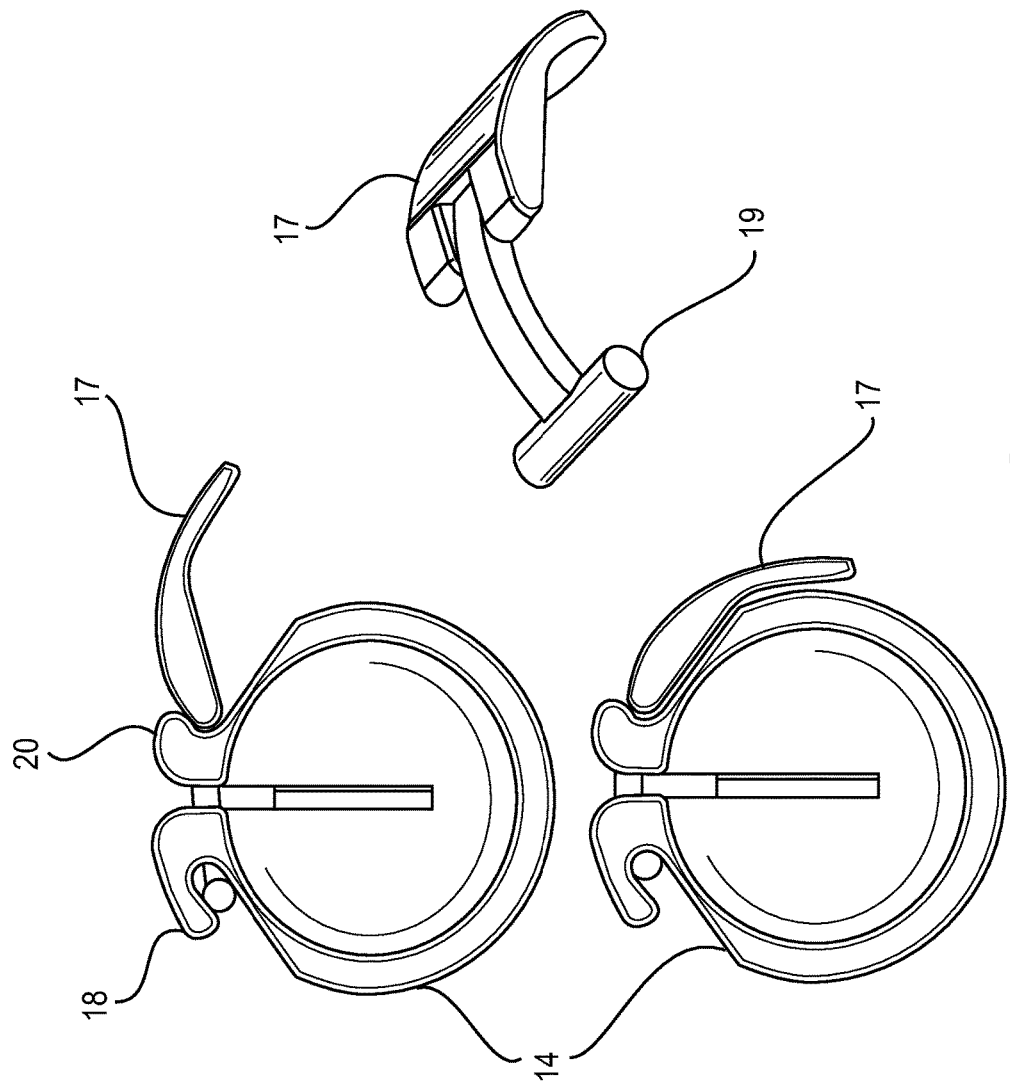
FIG. 7B depicts a component of the joint of FIG. 7A in both an open position and a closed position, according to an embodiment of the present disclosure.
Figure 7A:
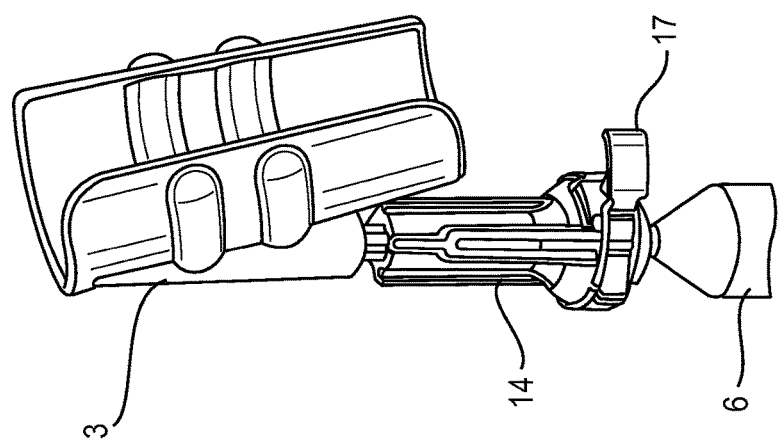
FIG. 7A illustrates an exemplary portion of a joint, according to an embodiment of the present disclosure.

In the embodiment of FIGS. 7A and 7B, instead of screw mechanism 13, a buckle 17 is used to clamp adapter 14 around ball 12. One side of the opening in recess 26 includes a hook 18, and the other side includes an engagement portion 20. A pin 19 of buckle 17 is positioned within hook 18, and buckle 17 is adjacent to engagement portion 20. When positioning adapter 14 on ball 12, buckle 17 is kept in an open configuration. Once in place, buckle 17 is then clamped shut, pulling pin 19 against hook 18 and pulling the two sides of the opening in recess 26 towards each other to clamp adapter 14 around ball 12. Again, buckle 17 should clamp adapter 14 around ball 12 tight enough to allow holder 3 to hold endoscope 2 in place and to provide free range of motion, but not so tight that the smoothness of adapter 14 moving around ball 12 is inhibited.

Alternatively, instead of including openings or slits in recess 26, adapter 14 or a wall of recess 26 may be deformable or compressible to achieve compression of adapter 14 around ball 12 when tightened.

In some embodiments, adapter 14 may include multiple engagement portions 20 or multiple hooks 18, and which engagement portion 20 or hook 18 is used for pin 19 or buckle 17 to move recess 26 to the closed configuration may affect the tightness of adapter 14 around ball 12 and, consequently, the resistance of adapter 14 around ball 12 to movement. In some embodiments, stand 10 may include one or more indicators, as described above, that convey to a user what level of resistance is achieved by using each engagement portion 20 or hook 18.

In the embodiment of FIGS. 8A-8C, adapter 14 may be clamped onto ball 12 using a locking nut 22. Like adapters 14 described above, adapter 14 of FIGS. 8A-8C includes one or more slits or openings in recess 26, which receives ball 12. To tighten adapter 14 around ball 12, a locking nut 22 may be pushed down over adapter 14. FIG. 8B depicts a cross-sectional view of holder 3 with locking nut 22 when recess 26 of adapter 14 is secured in place over ball 12. When fitting adapter 14 onto ball 12, locking nut 22 may be slid upwards so as to overlap less with the recess portion of adapter 14 that receives ball 12. Once adapter 14 is in place on ball 12, a user may force locking nut 22 down over the recess portion. An inner diameter of locking nut 22 may be smaller than an outer diameter of adapter 14 around ball 12 when adapter 14 is uncompressed. Thus, when locking nut 22 is moved downwards over adapter 14, the openings of adapter 14 are compressed together, securing adapter 14 and recess 26 to ball 12.

Locking nut 22 may be slid down over adapter 14 or may be screwed down over adapter 14. For example, in the embodiment shown in FIGS. 8B and 8C, adapter 14 includes threads 24 over which a portion of locking nut 22 must be passed. In some embodiments, locking nut 22 may include one or more corresponding protrusions configured to engage threads 24 as locking nut 22 is forced downwards over threads 24 and over adapter 14. In other embodiments, locking nut 22 may include complimentary threads so that locking nut 22 screws down in place over adapter 14.

Alternatively, instead of including openings or slits, recess 26 of adapter 14 or a wall of recess 26 may be deformable or compressible to achieve compression of adapter 14 around ball 12 during tightening.

In some embodiments, the extent to which locking nut 22 is forced downwards over adapter 14 may affect the resistance of adapter 14 around ball 12 to movement. Additionally or alternatively, a user may be able to adjust the resistance of stand 10 by moving locking nut 22. Stand 10 may include one or more visual, audible, or tactile indicators that may convey to a user the amount of resistance achieved by moving locking nut 22 to a certain position. Exemplary indicators may include increased resistance to tightening, clicks, markings on a portion of stand 10 (e.g., a gauge or ruler or marking indicating that when locking nut 22 is tightened to that position, a certain level of resistance is achieved), or other suitable indicators. In some embodiments, the indications may be staggered in a series to convey to the user when another level of resistance has been achieved.

Figure 9C:
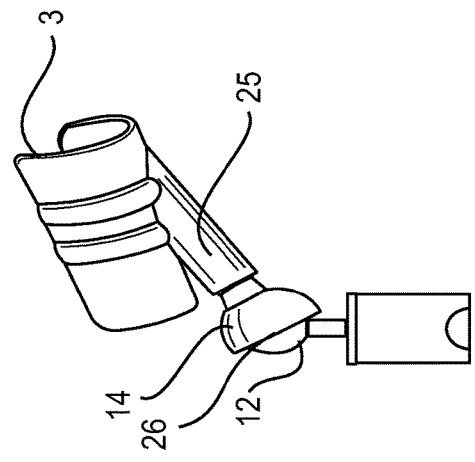
FIG. 9A illustrates an exemplary holder, according to an embodiment of the present disclosure.
FIG. 9B illustrates a joint, according to an embodiment of the present disclosure.
FIG. 9O illustrates a joint according to an embodiment of the present disclosure.
FIG. 9D illustrates two components in an unlocked position, according to an embodiment of the present disclosure.
FIG. 9E illustrates two components of the joint in a locked position, according to an embodiment of the present disclosure.
Figure 9E:
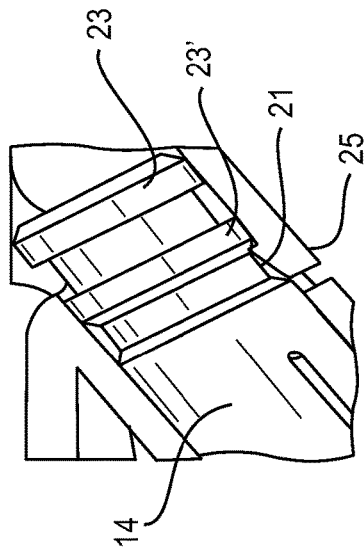
Figure 9B:
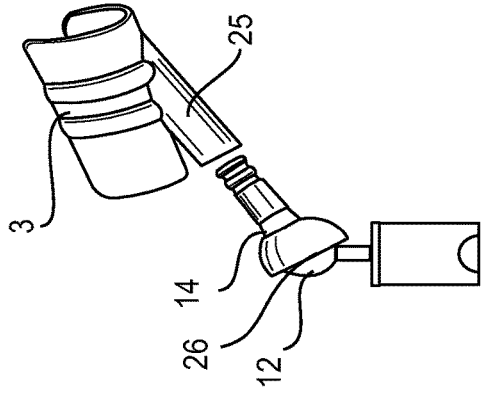
Figure 9D:
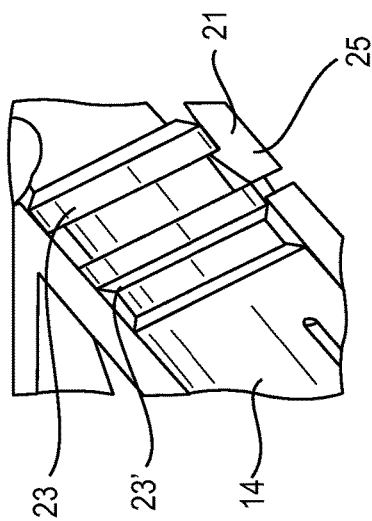
Figure 9A:
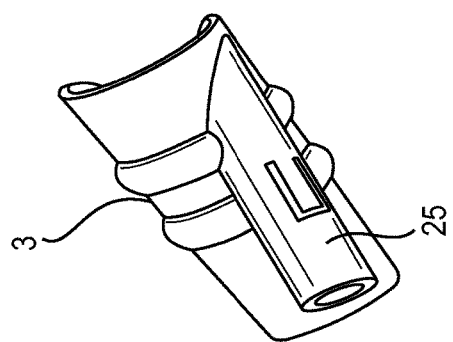

In the embodiment of FIGS. 9A-9E, instead of locking nut 22, a groove 25 in holder 3 may be configured to receive adapter 14 and to apply compression on adapter 14 once received. Adapter 14 may be separate from holder 3 (FIG. 9A) and may be positioned on ball 12 (FIG. 9B). Once recess 26 of adapter 14 is in place, groove 25 of holder 3 may then be positioned over adapter 14, compressing adapter 14 and recess 26 and securing adapter 14 to ball 12 (FIG. 9C), as described above in reference to the embodiment of FIGS. 8A-8C.

In some embodiments, adapter 14 is not be separate from holder 3 and instead may be movably coupled within groove 25. For example, adapter 14 may be positioned on ball 12 when holder 3 is in an unsecured position in which adapter 14 extends out further from groove 25. To secure adapter 14 to ball 12, a user may then push holder 3 down towards ball 12, forcing adapter 14 further inside groove 25 and into a secured position. For example, an inner surface of groove 25 may include a protrusion 21 configured to engage one or more flanges 23 of adapter 14. In the unsecured position (FIG. 9D), protrusion 21 may rest between flanges 23 and 23'. When the user applies a sufficient force to holder 3 to secure recess 26 of adapter 14 to ball 12, flange 23' may be forced upwards over protrusion 21 into a secured position (FIG. 9E). Additionally, flanges 23, 23' and protrusion 21 may also be used in the separated embodiments of FIGS. 9B and 9A in order to secure adapter 14 to ball 12 and/or to apply different levels of compression on adapter 14. One of ordinary skill in the art will recognize that different mechanisms may be used in addition to or instead of flanges and protrusions in order to provide similar function.

In some embodiments, groove 25 may include multiple protrusions 21, and a user may be able to increase or decrease the compression applied by adapter 14 on ball 12 by pushing or pulling holder 3 so that flange 23' is forced over more or fewer protrusions 21. In some embodiments, adapter 14 may include additional flanges 23 that may also pass over protrusion 21 to achieve additional tightening. In some embodiments, the extent to which groove 25 is forced downwards over adapter 14 may affect the resistance of adapter 14 around ball 12 to movement. Additionally or alternatively, a user may be able to adjust the resistance of stand 10 by moving groove 25. Stand 10 may include one or more visual, audible, or tactile indicators that may convey to a user the amount of resistance achieved by moving groove 25 to a certain position. Exemplary indicators may include increased resistance to tightening, clicks, markings on a portion of stand 10 (e.g., a gauge or ruler or marking indicating that when groove 25 is moved to that position, a certain level of resistance is achieved), or other suitable indicators. In some embodiments, the indications may be staggered in a series to convey to the user when another level of resistance has been achieved.

Figure 10B:
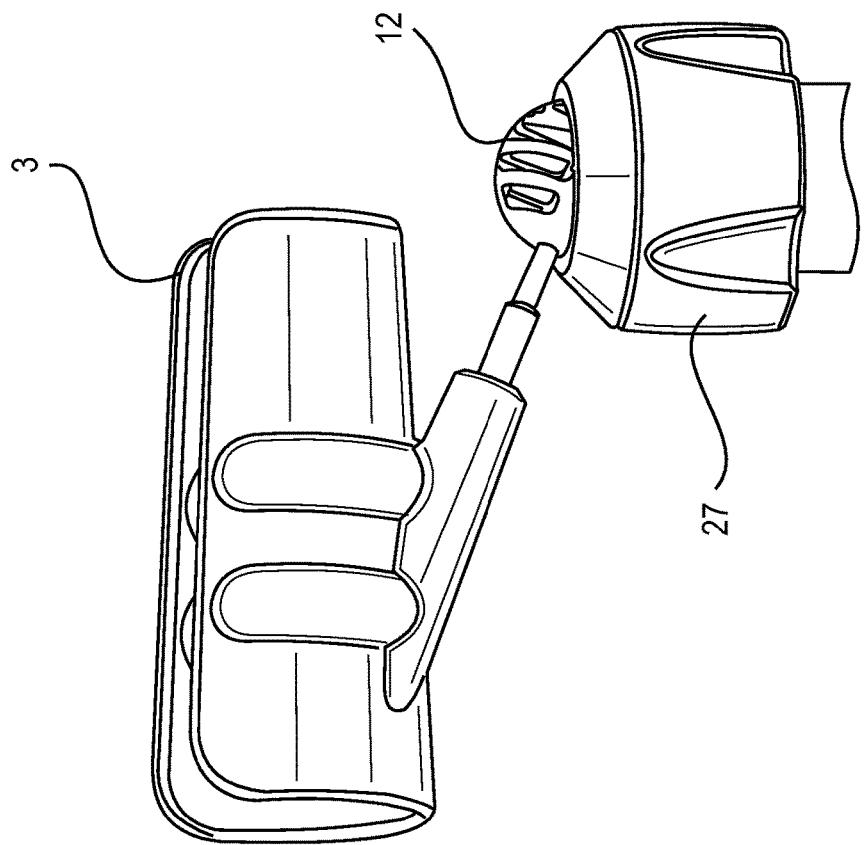
FIGS. 10A and 10B depict components of an exemplary joint, according to an embodiment of the present disclosure.
Figure 10A:
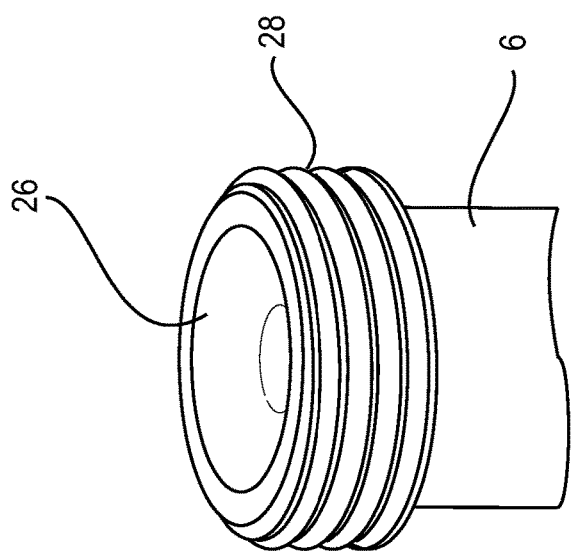

In the embodiment of FIGS. 10A and 10B, body 6 does not include ball 12. Instead, body 6 includes a recess 26 configured to receive a portion of ball 12, which is included as part of holder 3. Holder 3 is attached to a shaft that projects out of ball 12, as is shown in FIG. 10B, and, similar to the embodiment of FIGS. 8A-8C, discussed above, the embodiment of FIG. 10B includes a nut adapter 27 to fasten ball 12 and holder 3 onto body 6. Ball 12 of holder 3 is positioned in recess 26 of body 6. Once in place, nut adapter 27 may be fastened around body 6 to attach holder 3 to body 6 and secure and compress ball 12 in place.

In the exemplary embodiment, body 6 includes threads 28 by which a portion of nut adapter 27 is connected. In some embodiments, nut adapter 27 may include one or more corresponding protrusions configured to engage threads 28 as nut adapter 27 is forced downwards over threads 28 and onto body 6. In other embodiments, nut adapter 27 may include complimentary threads located on an inner surface so that nut adapter 27 screws in place onto body 6. In still other embodiments, nut adapter 27 may snap-fit, friction-fit, buckle, latch, lock, or otherwise secure in place to body 6.

In the embodiment of FIGS. 10C-10F, instead of threads 28, body 6 includes one or more radial pins. Nut adapter 27 includes one or more matching L-shaped slot(s), as shown in FIG. 10F, and the pins and slots mate with each other to mount holder 3 on body 6. When ball 12 is positioned within recess 26, the pins are aligned with a vertical portion of the L-shaped slot and then nut adapter 27 is twisted around base 6 so that the pins slide across a horizontal portion of the slot into a locked position. FIGS. 10D and 10E show the unlocked and locked positions, respectively.

In the embodiments of FIGS. 10A and 10B and 10C-10F, ball 12 may be included in holder 3 so that the resistance of ball 12 is fixed, and holder 3 is simply attached to body 6. Alternatively, securing holder 3 to stand 6 may increase the resistance of ball 12 upon tightening. For example, an upper portion of nut adapter 27 may have a smaller inner diameter than the rest of nut adapter 27, and as nut adapter 27 is tightened in place on body 6, ball 12 may be forced towards the portion of nut adapter 27 having a smaller diameter. In some embodiments, the extent to which nut adapter 27 is tightened onto body 6 may affect the resistance of ball 12 to movement. Additionally or alternatively, a user may be able to adjust the resistance of stand 10 by moving nut adapter 27. Stand 10 may include one or more visual, audible, or tactile indicators that may convey to a user the amount of resistance achieved by moving nut adapter 27 to a certain position, as described above in reference to locking nut 22.

In embodiments of FIGS. 10C-10F, nut adapter 27 may be designed to provide a fixed amount of resistance, or the L-shaped slot may provide adjustable resistance. For example, the slot may include a ramp or similar configuration that provides more resistance as nut adapter 27 is twisted further relative to base 6. Additional twisting may cause more compression to be applied to ball 12, creating more interference between ball 12 and nut adapter 27. In some embodiments, the ramp may include one or more steps. For example, a first step of the ramp may provide the lowest resistance, and each additional step may provide higher resistances. As described above, stand 10 may include one or more indicators to provide feedback to a user (e.g., tactile or auditory) regarding how much resistance is applied when nut adapter 27 is twisted to a given position.

The embodiment of FIGS. 11A and 11B depict a different variation of the embodiment of FIGS. 10A-10F that includes a separate connector 16. Connector 16 is positioned between body 6 and nut adapter 17 and may act a removable interface between body 6 and nut adapter 27. In FIGS. 11A and 11B, ball 12 is included as part of holder 3. A separate connector 16, which includes a recess 26, is removably fitted at the top of body 6. Once connector 16 is fitted in place on body 6 (e.g., snap-fit, screwfit, or friction-fit), ball 12 is nested into recess 26 and a nut adapter 27 is positioned over connector 16 so that an inner surface of nut adapter 27 engages with an outer surface of connector 16. Similar to FIGS. 10A-10F, the outer surface of connector 16 includes threads 28 over which a portion of the inner surface of nut adapter 27 is connected to body 6. In some embodiments, the inner surface of nut adapter 27 may include one or more corresponding protrusions configured to engage threads 28 of connector 16 as nut adapter 27 is forced downwards over threads 28 and onto body 6. In other embodiments, the inner surface of nut adapter 27 may include complimentary threads so that nut adapter 27 screws down in place onto connector 16 and thus body 6. In still other embodiments, nut adapter 27 may snap-fit, friction fit, buckle, latch, lock, or otherwise secure in place onto connector 16 and/or body 6. Once nut adapter 27 is connected in place on connector 16, ball 12 is compressed within recess 26, as shown in FIG. 11B, and holder 3 is connected to body 6. In other embodiments, connector 16 may fit inside of an upper hollow portion of body 6 to receive ball 12 in recess 26, and nut adapter 27 may contact body 6, rather than connector 16, to attach holder 3 to body 6.

By including a separate connector 16, the embodiment of FIGS. 11A and 11B may facilitate cleaning of stand 10 in between uses. For example, if body 6 and base 7 are reusable, connector 16 may cover an upper portion of body 6 that may be more likely to become soiled during use. In some embodiments, incorporating threads 28 onto connector 16 instead of on body 6 may make body 6 easier to clean. Connector 16 may attach to a solid portion of body 6 having smooth surfaces that are easier to wipe down and disinfect. In embodiments in which body 6 is hollow, connector 16 may also inhibit debris from getting inside of body 6 when connecting and/or disconnecting holder 3, again making body 6 easier to clean. Connector 16 and/or holder 3 may be removed and sterilized between procedures, or they may be disposable.

In the embodiment of FIGS. 12A-12C, ball 12 is received within a deformable cuff 33. Cuff 33 may be formed of a suitable deformable material, including, e.g., nylon, plastic, or a thin, flexible metal. When seated in cuff 33, ball 12 may compress against a friction pad 29, shown below ball 12 in FIG. 12C. Friction pad 29 may be a compressible pad of any suitable size or thickness formed of, e.g., rubber, plastic, foam, silicone, cloth, or other suitable material. A spring 36 may be oriented below friction pad 29 to exert an upwards compression force on friction pad 29.

As nut adapter 27 is tightened over threads 28 (similar to FIGS. 11A and 11B, discussed above), an inner diameter of nut adapter 27 may apply a compression force on cuff 33, causing cuff 33 to deform inwards towards ball 12 to increase the pressure exerted on ball 12 (similar to what is described in reference to FIGS. 10A and 10B). As nut adapter 27 is tightened, ball 12 and cuff 33 may be forced down towards body 6, pushing ball 12 against friction pad 29 and pushing friction pad 29 against spring 36. As friction pad 29 pushes further against spring 36, spring 36 applies an increasing compressive force upwards onto friction pad 29. Accordingly, as nut adapter 27 is tightened, additional forces may be exerted onto ball 12, and the resistance to movement of ball 12 may be increased. In some embodiments, a user may be able to adjust the resistance of stand 10 by moving nut adapter 27. Stand 10 may include one or more visual, audible, or tactile indicators that may convey to a user the amount of resistance achieved by moving nut adapter 27 to a certain position, as described above in reference to nut adapter 27 and locking nut 22.

In some embodiments, ball 12, nut adapter 27, cuff 33, friction pad 29, and spring 36 may be incorporated as a unit that is part of holder 3. The portion in which spring 36 is contained may fit into an upper portion of stand 6, and nut adapter 27 may interact with an outer surface of stand 6. In other embodiments, one or more of spring 36, friction pad 29, cuff 33, and/or nut adapter 27 may be part of stand 6 and ball 12 may be part of holder 3. The portions incorporated with holder 3 may be disposable or may be capable of being sterilized, e.g., formed of materials that are suitable for withstanding an autoclave.

Figure 13B:
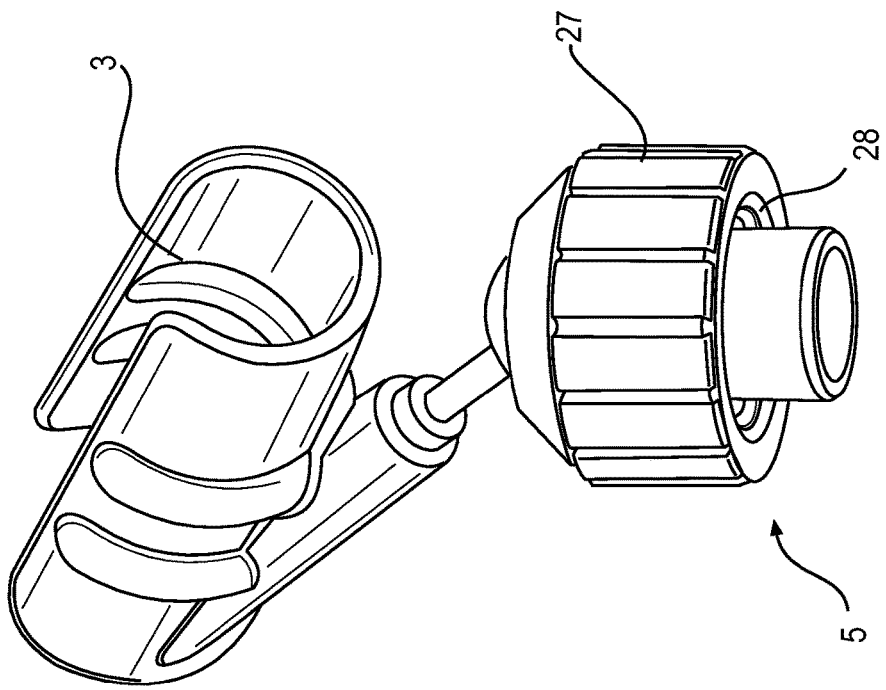
FIG. 13B depicts a preassembled assembled joint, according to an embodiment of the present disclosure.
Figure 13A:
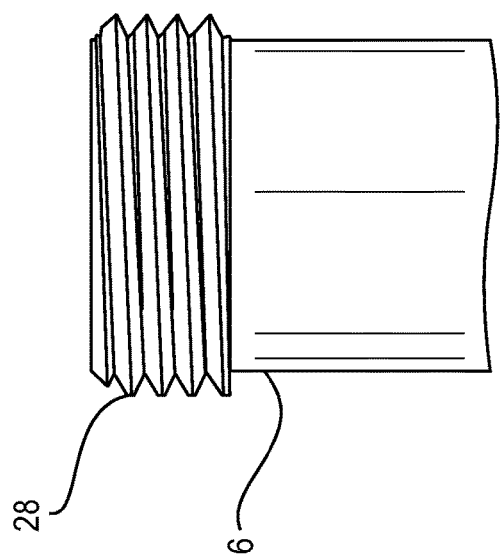
FIG. 13A depicts a receiving portion for a preassembled joint, according to an embodiment of the present disclosure.
Figure 13C:
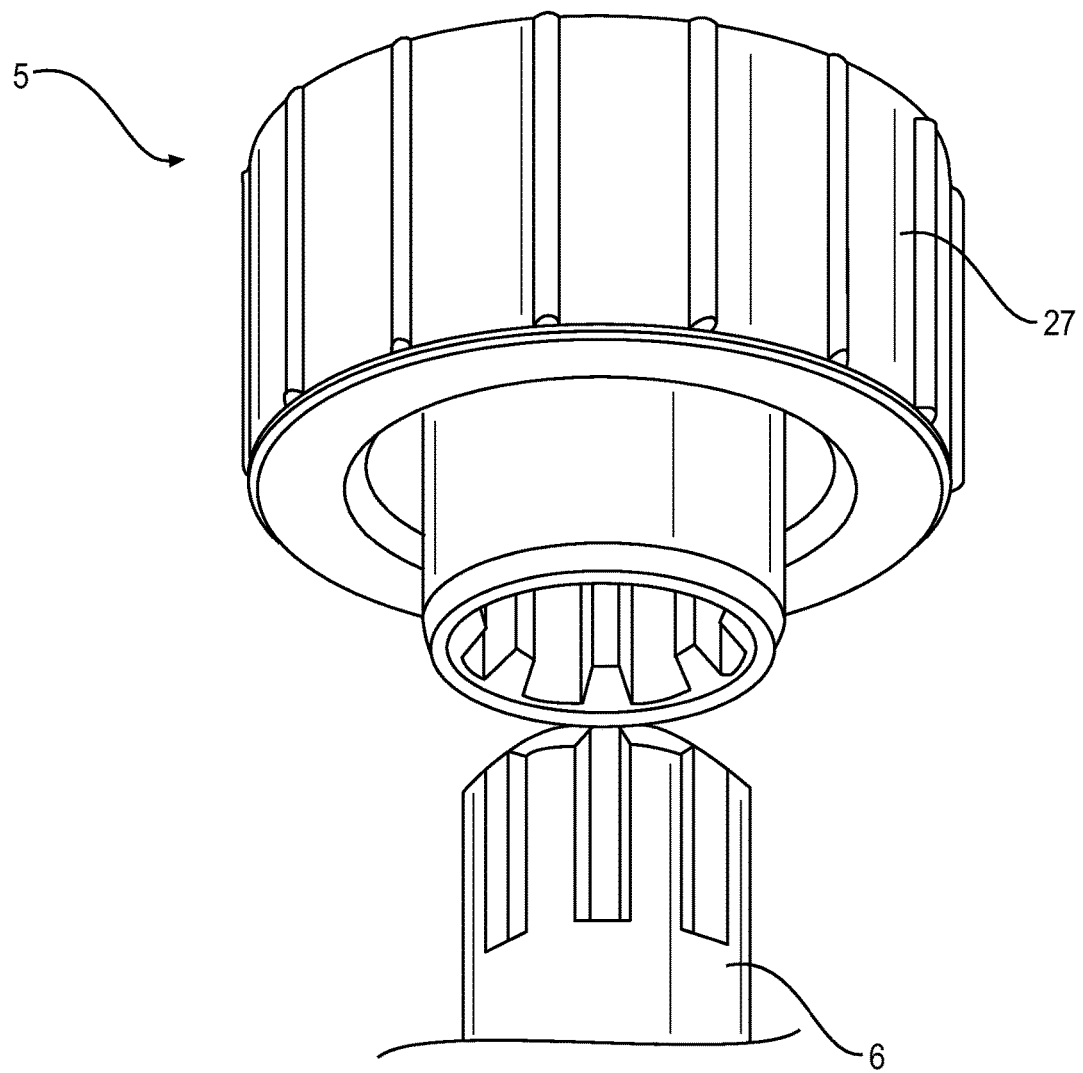
FIG. 13C depicts a preassembled joint, according to another embodiment of the present disclosure.

In the embodiment of FIGS. 13A and 13B and the embodiments of FIGS. 13C and 13D, joint 5 is preassembled and fully included as part of holder 3. Both the recessed portion 26 and ball 12 are included in holder 3. In the exemplary embodiment of FIG. 13A, body 6 includes threads 28 to attach joint 5 of holder 3 onto body 6. In some embodiments, an inner surface of nut adapter 27 or joint 5 may include one or more corresponding protrusions configured to engage threads 28 as preassembled joint 5 is forced downwards over threads 28 and onto body 6. In other embodiments, nut adapter 27 or joint 5 may include complimentary threads so that preassembled joint 5 screws down in place onto body 6. In the embodiment of FIGS. 13C and 13D, body 6 includes one or more grooves configured to mate with one or more corresponding protrusions located on an inner surface of nut adapter 27 or joint 5 as preassembled joint 5 is moved into position on body 6. Alternatively, body 6 may include one or more protrusions and preassembled joint 5 may include one or more corresponding grooves, or a combination thereof. Alternatively, as is described in reference to FIGS. 10A and 10B, holder 3 with joint 5 may be secured to body 6 via snap-fit, friction fit, buckle, latch, lock, or in any other suitable manner. Also as described in reference to FIGS. 10A and 10B, the resistance of ball 12 to movement may be fixed in preassembled joint 5 or may be variable.

Figure 14B:
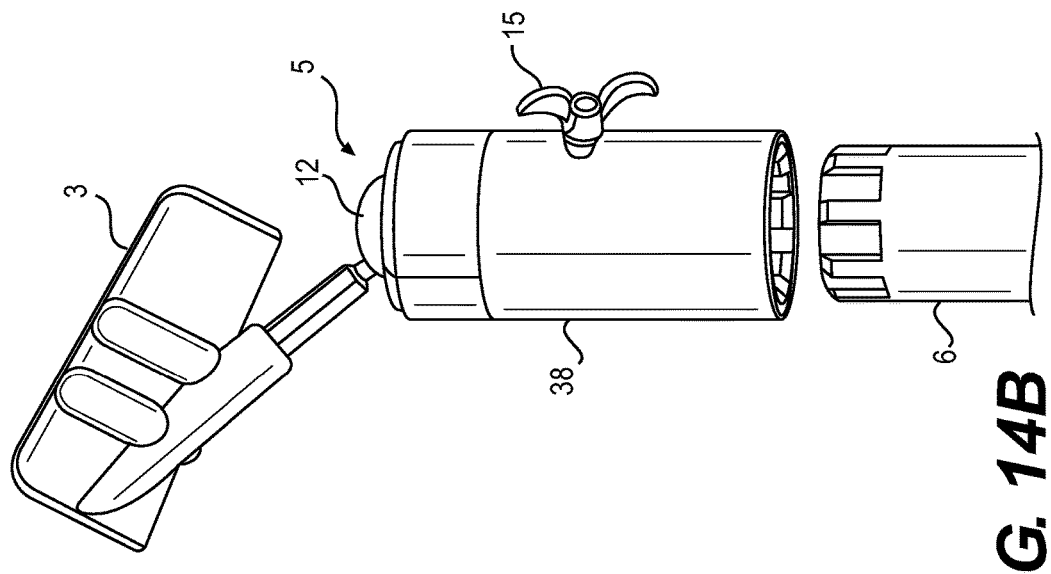
FIGS. 14A and 14B depict a preassembled assembled joint, according to another exemplary embodiment of the present disclosure.
Figure 14A:
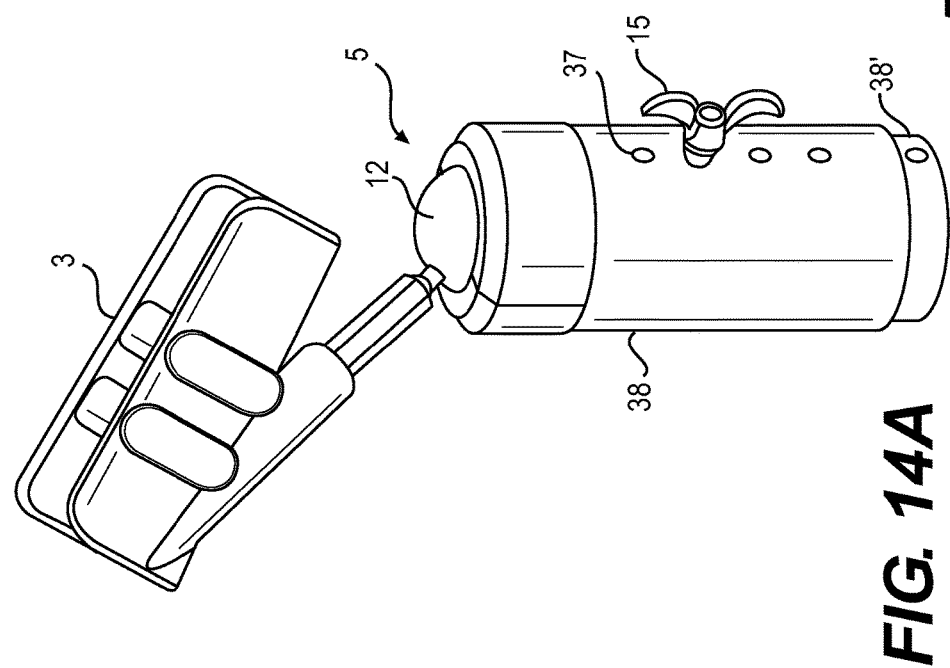

Another embodiment of a preassembled joint integrated as part of holder 3 is shown in FIG. 14. An adjustable sliding collar 38 fits onto a top portion of body 6 and applies a compression force to ball 12 as it is fastened to body 6, as described above in reference to the previous embodiments. Collar 38 may allow a user to adjust the compressive force applied by collar 38 on ball 12 to adjust the resistance to movement of ball 12. In some embodiments, wingnut 15 can be tightened through an opening 37 in collar 38 to allow collar 38 to be moved over more or less of body 6 to adjust the compressive force applied to ball 12, and, as a result, the resistance. Wingnut 15 may be loosened to allow collar 38 to move freely up or down relative to body 6, or may be tightened so that wingnut 15 interacts with an underlying portion of body 6 to lock collar 38 in place at a given resistance. Body 6 may include groves, protrusions, or openings on an outer surface configured to interact with wingnut 15 or collar 38 to allow a user to position collar 38 in a given position. In some embodiments, joint 5 may further include an inner collar 38' over which collar 38 slides. Wingnut 15 may interact with grooves or openings on an outer surface of inner collar 38' instead of an outer underlying surface of body 6. In such an embodiment, inner collar 38' may be screw-fit, friction-fit, or snap-fit, e.g., onto body 6, and collar 38 may slide relative to inner collar 38' to adjust the resistance of joint 5.

In place of a wingnut 15, a spring-actuated button may protrude out from body 6 or inner collar 38'. Outer collar 38 may include a plurality of openings 37, and the button may be compressed to allow collar 38 to freely slide over body 6 or inner collar 38'. Each opening 37 may correspond with a certain level of resistance, and the opening corresponding to the desired level of resistance may be positioned over the button. The button may be released and allowed to extend through the desired opening 37. Any other suitable mechanisms may be used to adjust the resistance and/or attach a preassembled joint 5 to body 6.

Or, in some embodiments, tightening wingnut 15 may cause collar 38 to increase the compressive force applied to ball 12 while collar 38 remains in place. In the embodiment of FIG. 14, body 6 includes one or more grooves configured to mate with one or more corresponding protrusions located on an inner surface of collar 38 as preassembled joint 5 is moved into position on body 6. Alternatively, body 6 may include one or more protrusions and preassembled joint 5 may include one or more corresponding grooves, or a combination thereof. Wingnut 15 may allow a user to position collar 38 along the length of these grooves to achieve different levels of resistance or may apply a compressive force to ball 12 while collar 38 remains in place.

In the embodiments described in relation to FIG. 14, the resistance of ball 12 to movement in joint 5 may be fixed or adjustable. Additionally, stand 10 may include one or more visual, audible, or tactile indicators, as described previously. The preassembled joints described herein may be disposable or may be capable of being sterilized, e.g., formed of materials that are suitable for withstanding an autoclave.

As is described above, ball 12 and/or the tightness of adapter 14 or other components around ball 12 may affect the resistance to movement of stand 10. Stand 10 may also be configured to affect the resistance to movement in other ways, too. For example, ball 12 may include one or more coatings, e.g., a lubricious, textured, or smooth coating configured to increase or decrease resistance to movement or to promote even motion of ball 12 and/or adapter 14. Alternatively or additionally, a portion of the surface of ball 12 or a portion of ball 12 may be formed of a different material or may have a different texture (e.g., grooves or ridges) or different coefficient of friction. In some embodiments, the different surface configurations and/or coatings may allow adapter 14 to more securely grip ball 12 or may limit the range of motion of ball 12 and/or adapter 14 or may provide tactile feedback to a user regarding the positioning of joint 5 when moving endoscope 2 on stand 10. Ball 12 may also include a visual indicator, such as rings, markings (e.g., colors), etc., to indicate the range of motion of ball 12 and/or to indicate when a user is approaching the limit of ball 12's range of motion in a given direction.

In some embodiments, the surface area of components that contact ball 12 (e.g., adapter 14, recess 26, locking nut 22, nut adapter 27, etc.) may be shaped or sized to affect movement of joint 5. For example, increasing the contact area between the components may increase the resistance, or the components may include rims, ridges, or treads to affect movement. In some embodiments, the shapes of the components that receive ball 12 (e.g., recess 26) may not be perfectly circular and may resist movement more in certain directions, for example.

Figure 15C:
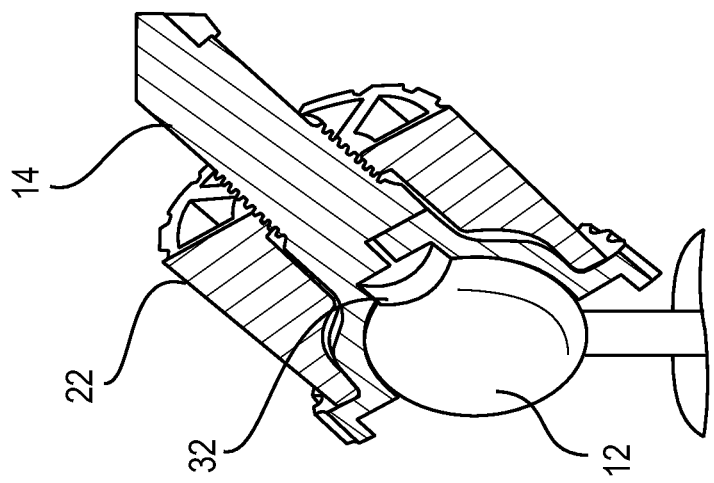
FIG. 15C depicts a partial, cross-sectional view of a joint having an interface, according to an embodiment of the present disclosure.
Figure 15B:
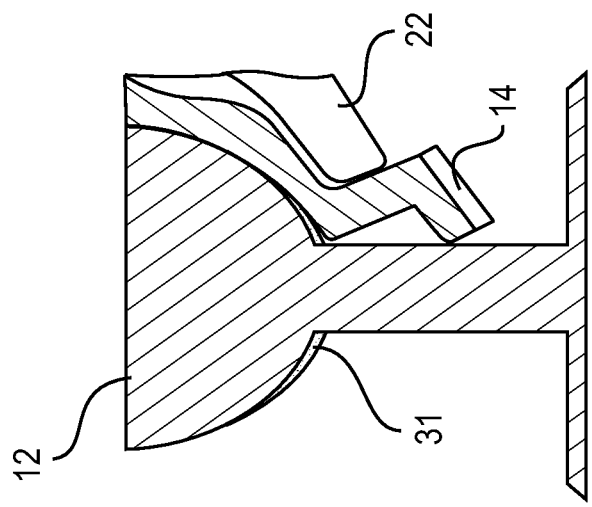
FIG. 15B depicts a cross-sectional view of the joint of FIG. 15A, according to an embodiment of the present disclosure.
Figure 15A:
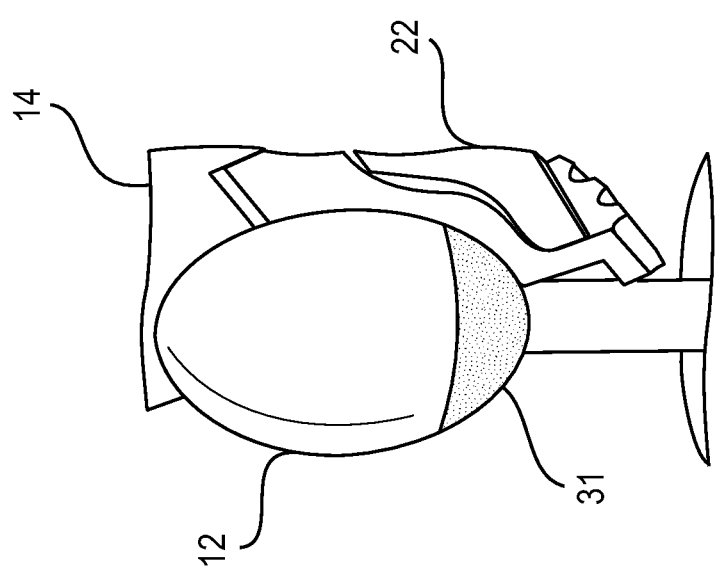
FIG. 15A depicts a partial, cross-sectional view of a joint having a modified surface, according to an embodiment of the present disclosure.

As is shown in FIGS. 15A and 15B, ball 12 may include a modified surface 31 located on a lower region of ball 12 near body 6, although modified surface 31 may be of any suitable shape or size and may be included on any portion of ball 12, for example, depending on the purpose of modified surface 31. In some embodiments, multiple discrete areas of modified surface 31 may be included. In some embodiments, modified surface 31 may be included on a recess 26 of adapter 14 configured to interface with ball 12, or may be included on both ball 12 and recess 26. Although FIGS. 15A and 15B depict an embodiment for use with an adapter 14 and locking nut 22, modified surface 31 may be used in conjunction with any of the disclosed configurations of joint 5, including those related to the embodiments of 3B and 3C.

In some embodiments, as shown in FIG. 15C, ball 12 and adapter 14 may include an interface 32 configured to provide cushioning between ball 12 and adapter 14, to affect range of motion of adapter 14 and/or ball 12, to increase or decrease resistance to movement, or to promote even motion of adapter 14 and/or ball 12. Interface 32 may be formed of any suitable material, e.g., rubber, plastic, foam, silicone, cloth, etc., and may be of any suitable shape or size. For example, interface 32 may be formed as a washer or ring around a portion of ball 12, or a pad of any suitable size or thickness. In some embodiments, multiple discrete interfaces 32 may be included. In some embodiments, interface 32 may be separate from ball 12 and adapter 14, may be included on an inner surface of adapter 14 configured to interface with ball 12 (e.g., recess 26), may be included on an outer surface of ball 12 configured to interface with adapter 14, or may be included on both ball 12 and adapter 14. Although FIGS. 15A and 15B depict an embodiment for use with a locking nut 22 and adapter 14, interface 32 may be used in conjunction with any of the disclosed configurations of joint 5 (e.g., nut adapter 27, collar 38, connector 16, etc.), including those related to the embodiments of 3B and 3C.

As mentioned above, joint 5 may be configured to provide a smooth range of motion for moving endoscope 2 on stand 10, but when endoscope 2 is not being held or manipulated by the physician, stand 10 is configured to keep endoscope 2 in position when the physician lets go. The insertion tube and/or umbilical cord may create a center of gravity and weight distribution that is inconsistent or awkward to counterbalance as endoscope 2 is moved. The weight of endoscope 2, including the insertion tube and/or umbilical cord, generates a moment around joint 5. Therefore, certain forces may be required at joint 5 to compensate the changing weight distribution and moment and to keep endoscope 2 in its position once a physician lets go.

As the angle between the z (vertical) axis and the axis of endoscope 2 on stand 10 is increased, a higher moment is created around ball 12. Maximum moment is created when endoscope 2 is in a horizontal position on stand 10. In a horizontal position, the moment generated by endoscope 2 may range, for example, from approximately 0.6 newton metres (Nm) to approximately 3 Nm. The required level of compression exerted on ball 12 is a function of the weight of endoscope 2, the distance between the center of the mass of endoscope 2 from the center of ball 12, the diameter of ball 12, and a friction coefficient of ball 12 and the portion of stand 10 (e.g., body 6, holder 3, or joint 5) configured to receive ball 12. One of ordinary skill in the art will recognize that the required clamping force applied to ball 12 will vary since the diameter of ball 12, the moment arm, and coefficient friction can vary, depending on the design of stand 10. For practical purposes, in some embodiments, the diameter of ball 12 may range from approximately 0.5 inches to approximately 3 inches.

Figure 16:
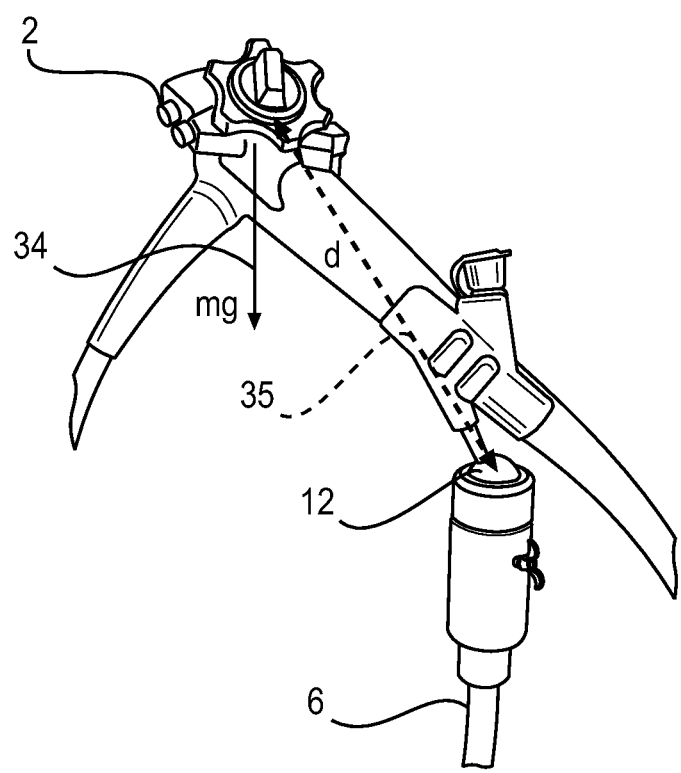
FIG. 16 depicts an endoscope positioned on a stand, according to an embodiment of the present disclosure.

To illustrate this, FIG. 16 depicts an exemplary embodiment of stand 10 with endoscope 2 positioned in holder 3. The moment ('M') of gravity force is expressed by the equation M=(mg)×d, where 'm' is the mass of endoscope 2, 'g' is the gravity acting on endoscope 2 (9.8 m/s$^2$) and 'd' is equal to the distance between the center of mass of endoscope 2 from the center of ball 12. Mass multiplied by gravity equals the weight of endoscope 2 on stand 10, which is indicated by arrow 34 in FIG. 16 representing this downward force. Line 35 indicates the distance 'd' in this exemplary embodiment. The resistance to movement created by joint 5 should compensate for the moment created by endoscope 2 when mounted on stand 10 so that the endoscope stays in place when a user lets go of the endoscope. The compressive force of ball 12 is a function of the radius of ball 12 and the coefficient of friction between ball 12 and recess 26. As described above, the different embodiments may provide a fixed resistance to account for the momentum created by endoscope 2 in any position or may allow a user to adjust the level of resistance.

Accordingly, embodiments of stand 10 are designed so that the size and shape of holder 3, the distance of holder 3 relative to ball 12, the fit of adapter 14 or other components around ball 12, the radius of ball 12, and the coefficient of friction of ball 12 and surrounding components in stand 10 can accommodate the various sizes, shapes, and weights of endoscopes 2, which may all affect the amount of movement and rotation allowed by stand 10, and, consequently, the different positions that endoscope 2 can be moved into while supported on stand 10.

As described previously, joint 5 provides motion in three planes, xy, xz, and yz. The range of motion may be between approximately 0-180 degrees, or more, in the y-z and x-z planes and between approximately 0-360 degrees, or less, in the x-y plane.

Figure 17A:
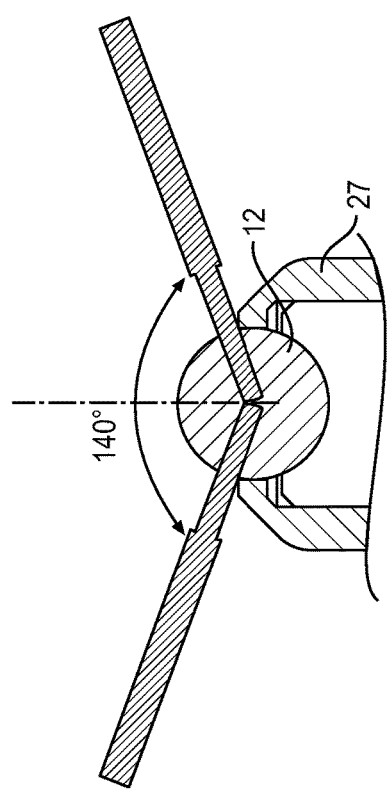
FIG. 17A depicts an exemplary range of motion of a stand, according to an embodiment of the present disclosure.
Figure 17B:
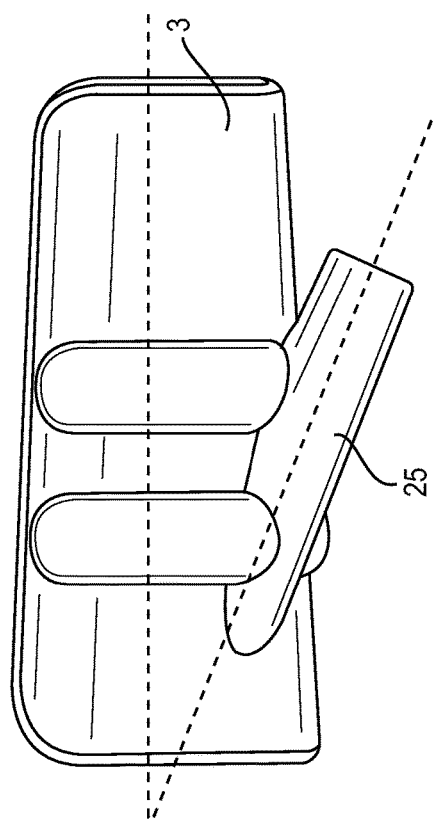
FIG. 17B depicts an exemplary holder, according to an embodiment of the present disclosure.
Figures 18A, 18B, 18C, 18D:
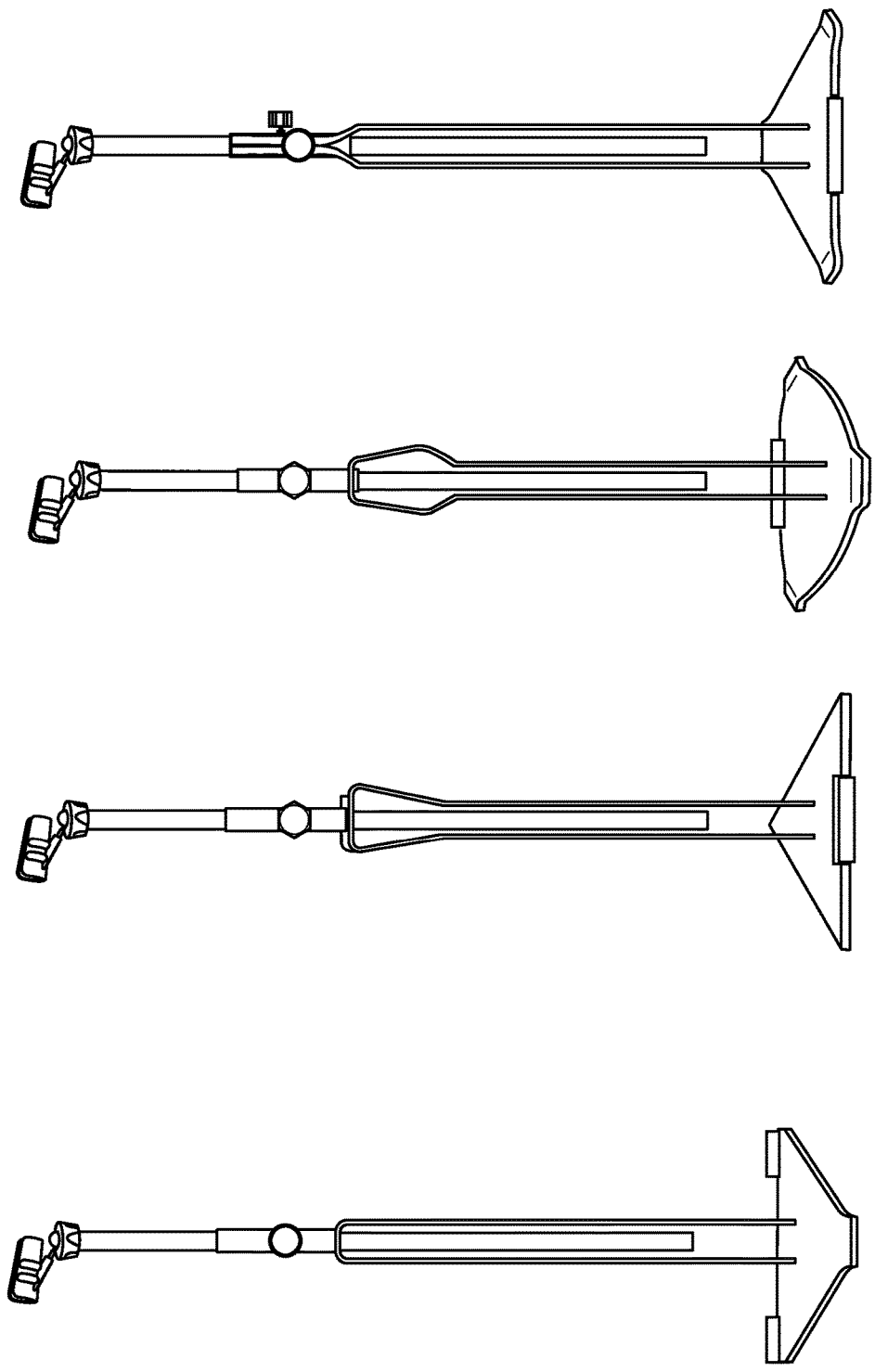
FIGS. 18A-18H depict exemplary stands, according to embodiments of the present disclosure.
Figure 18H:
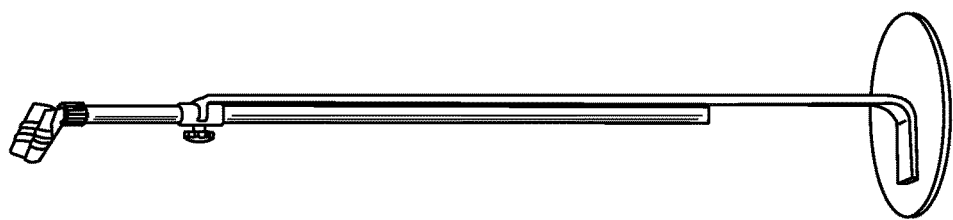
Figure 18G:
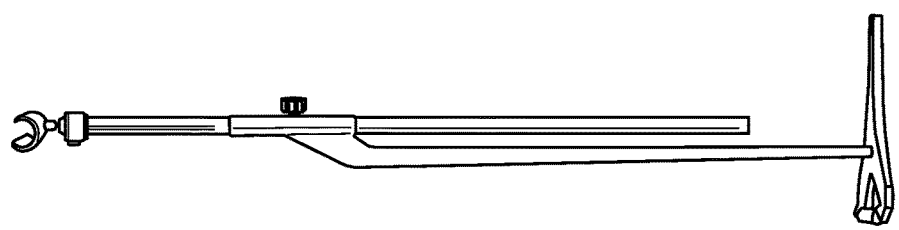
Figure 18F:
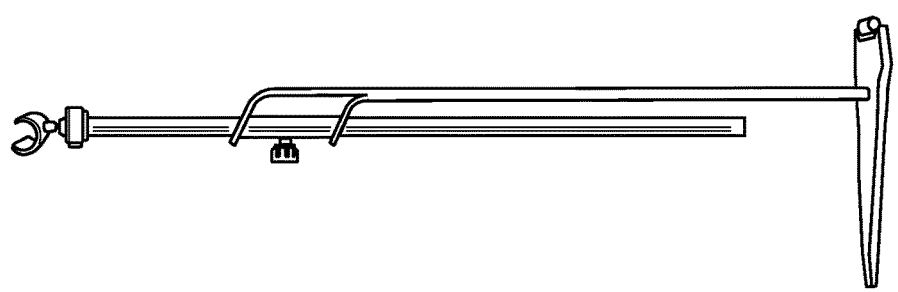
Figure 18E:
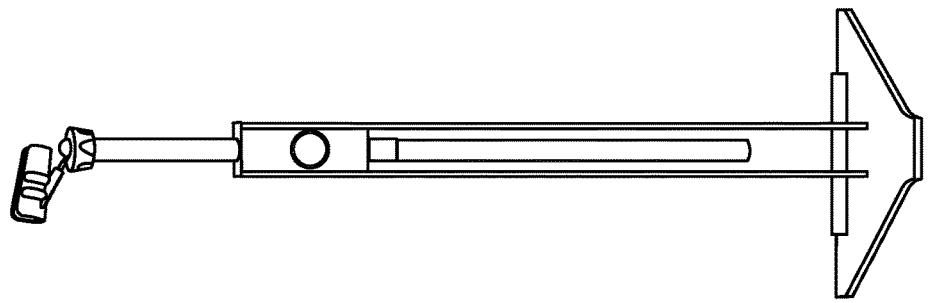

In the exemplary embodiment depicted in FIG. 17A, the range of motion of stand 10 in yz and xz planes is between approximately 0-140 degrees. While the range of motion of stand 10 may limit the range of motion of endoscope 2 on stand 10, stand 10 may in some embodiments be configured to allow greater range of motion of endoscope 2 than that of ball 12. For example, as is shown in FIG. 17B, groove 25 may connect holder 3 to ball 12 at an angle that is different from the angle at which endoscope 2 is held in holder 3. In other words, holder 3 may not hold endoscope 2 exactly parallel to the shaft extending out of ball 12 to which holder 3 attaches. By adjusting the angle between the axis of groove 25 and the axis along which endoscope 2 is held in holder 3, stand 10 may provide a greater or more restricted range of motion for endoscope 2 than for ball 12. For example, increasing the angle may allow endoscope 2 to extend further off axis than the ball shaft shown in FIG. 17A, and decreasing the angle between the two axes may bring the range of motion more in line with that of ball 12. In the embodiments of FIGS. 17A and 17B, a user can still position endoscope 2 horizontally, even though ball 12 provides a range of motion that is less than 180 degrees, as is shown in FIG. 17C.

Stand 10 may also be designed so that after the scope is placed inside holder 3, the range of motion achieved by endoscope 2 is substantially symmetrical along the y-z and/or x-z planes, or the range of motion in the y-z and/or x-z planes may not be symmetrical when the scope is in use (as is shown in FIGS. 17C and 17D). In the exemplary embodiments of FIGS. 17C and 17D, stand 10 is designed so that the ranges of motion is asymmetrical. This may be due to the angle between the axis of groove 25 and the axis along which endoscope 2 is held in holder 3 or may be the result of a separate design modification, for example, a physical barrier or limit to motion in a given direction. As is shown in the embodiments of FIGS. 17C and 17D, while stand 10 may still allow for a range of motion between approximately 0-360 degrees in the x-y plane, the range of motion may not be symmetrical in the y-z and/or x-z planes.

Also, stand 10 may provide additional axial motion around the axis of holder 3, which may also affect the range of motion achieved by endoscope 2. Holder 3 may rotate relative to joint 5 with a resistance that is different than the resistance of ball 12 in the ball joint. This rotational motion may be created by rotation of ball 12, rotation of the ball shaft relative to ball 12, rotation of the ball shaft relative to holder 3, or rotation holder 3 relative to the ball shaft. This axial motion could be free rotation (360 degrees) or may be more limited. In some embodiments, the resistance of rotation in this axial direction may be different than the resistance of movement of ball 12 in the other planes and may be independent from movement of ball 12. For example, because the resistance of ball 12 in joint 5 may be higher to offset the moment created by endoscope 2 on stand 10 in order to hold endoscope 2 in place when released, it may be more difficult for the user to freely rotate endoscope 2 by moving the smaller wrist muscles using only joint 5. This additional rotation along the axis of holder 3 may allow a user to more easily position endoscope 2 with the flex of a wrist at a decreased resistance.

Each of these design choices discussed above may affect the moment caused by endoscope 2 on stand 10 and thus the resistance to motion needed for ball 12 and consequent compressive force, or range of compressive forces, that is applied to ball 12 by joint 5.

Further, Body 6 of stand 10 is designed to support endoscope 2, to facilitate comfortable use of endoscope 2, and to facilitate easy cleaning and disinfection between use. Each of these features is described in greater detail below.

Body 6 preferably has a streamlined design so that stand 10 interferes as little as possible with the movement of endoscope 2 on stand 10 and the movement of medical staff around stand 10, including the movement of the physician manipulating endoscope 2. Body 6 may also have an adjustable height so that a user can position stand 10 to accommodate the height of the physician when seated or standing, the location of the patient, the size of the endoscope being used, the type of procedure being performed, or to otherwise achieve a comfortable height of endoscope operation. For example, in some embodiments, stand 10 may be adjustable to a height of as low as approximately 40 cm and a height as high as approximately 180 cm, or higher. In some embodiments, the height of stand 10 may be adjustable in a range of approximately 70 cm to 140 cm.

While most stands utilize telescoping parts to adjust height while maintaining a low profile, body 6 may not include telescoping parts or may include fewer telescoping or concentric portions. This is because body 6 and stand 10 may be reusable, and telescoping or concentric parts may be more difficult to clean. A reusable stand will need to be reprocessed for cleaning between procedures, and common telescopic shafts have gaps between the telescopic parts that can collect bacteria. Often the only way to reprocess and clean two telescoping portions would be to completely disassemble the stand. Even when the pieces are taken apart, the inner hollow portions may be difficult to reach, and even when broken down, these pieces may be too big to fit into a traditional autoclave of sterilization machine. Additionally, when telescoping portions pass by one another, one soiled section may transfer unclean materials and bacteria to other sections, spreading the unclean materials to other portions of the stand.

Figure 20B:
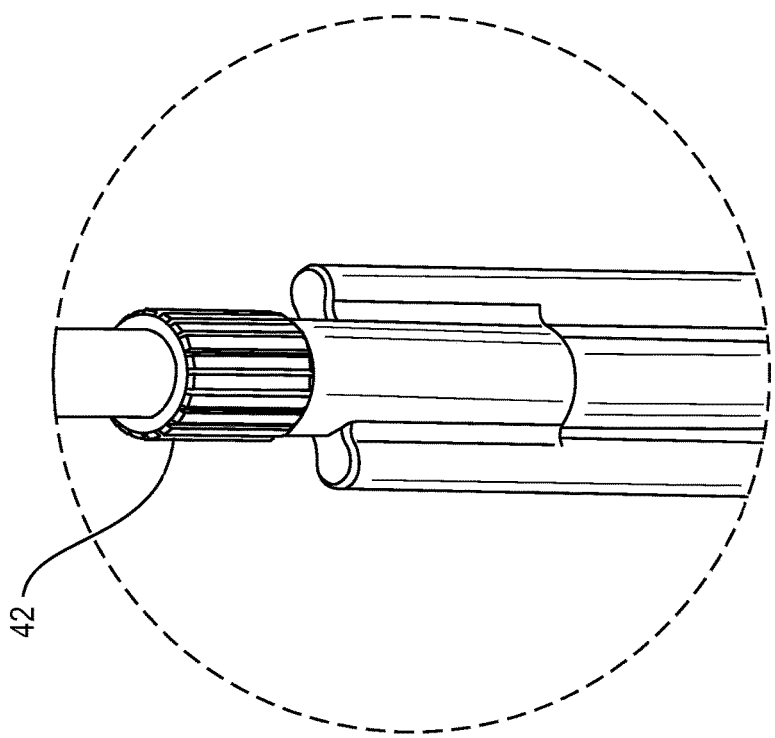
FIG. 20B depicts an adjustable portion of the stand of FIG. 20A, according to an embodiment of the present disclosure.
Figure 20A:
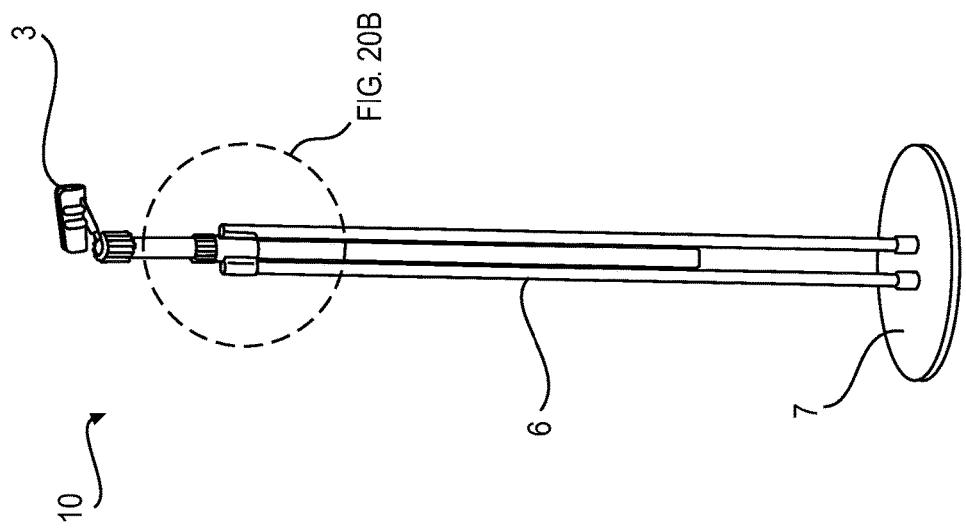
FIG. 20A depicts an exemplary stand, according to an embodiment of the present disclosure.

In the exemplary embodiments described herein, the surfaces of body 6 may be easier to access and clean and may not need to be disassembled for cleaning. FIGS. 18A-18H depict some exemplary stands 10 that have streamlined profiles and adjustable heights and include fewer telescoping portions. In the embodiments of FIGS. 18A-18H, the height of body 6 is adjusted using a knob 40. As depicted in FIG. 19, knob 40 is located over a region of body 6 that does include a telescoping portion. As is known in the art, knob 40 can be turned to free the telescoping portion of body 6, allowing it to be adjusted, and once the height is adjusted, knob 40 can be turned to tighten and hold the telescoping portion in place. By reducing the portion of body 6 that telescopes, cleaning stand 10 between procedures may be made easier. The central portion of stand 6 can be removed after use and wiped down, and the smaller hollow section that knob 40 is mounted on can be accessed more easily. In some embodiments, in place of knob 40, stand 10 may include a collet 42 (FIGS. 20A and 20B), which may be turned to adjust the height of body 6. Any other suitable mechanism may be used to achieve the function of knob 40 or collet 42.

Figure 21C:
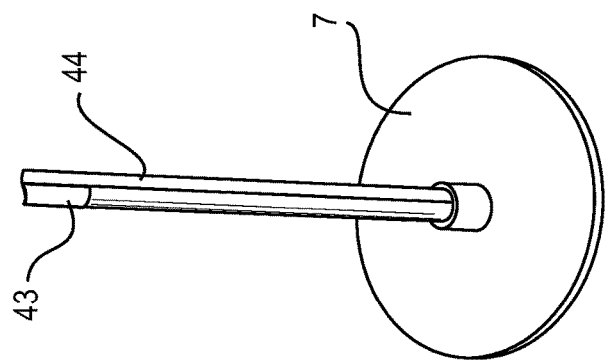
FIG. 21C depicts a lower portion of the stand of claim 21A, according to an embodiment of the present disclosure.
Figure 21B:
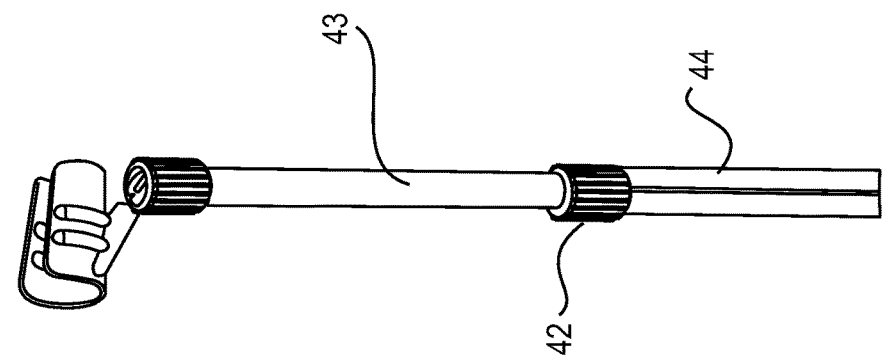
FIG. 21B depicts an adjustable portion of the stand of FIG. 21A, according to an embodiment of the present disclosure.
Figure 21A:
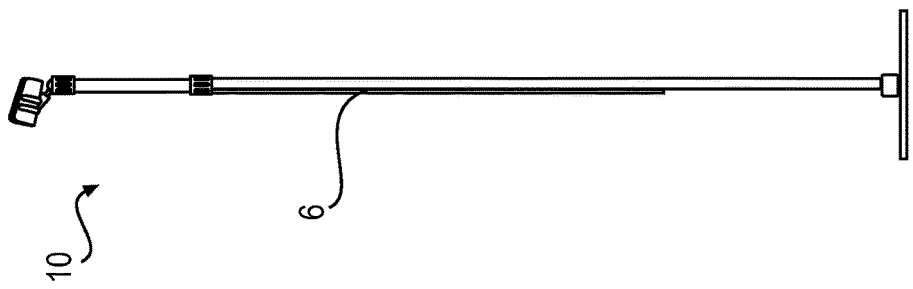
FIG. 21A depicts an exemplary stand, according to an embodiment of the present disclosure.

In the embodiment of FIGS. 21A-21C, stand 10 may look more like a traditional telescoping stand, but instead of one hollow tubular portion receiving another tubular portion within it, body 6 may be formed of a half-tube 44 configured to receive a tubular portion 43 within it. As described above and known in the art, upon loosening collet 42 (or a knob or other suitable tightening mechanism), tubular portion 43 may be adjusted up and down to a desired height. Once the desired height is reached, collet 42 may be tightened, locking the stand at the desired height. To clean stand 10, tubular portion 43 may be pulled up and out of engagement with collet 42 and half-tube 44, and the surface of tubular portion 43 may be wiped down. Unlike with standard telescoping stands, half-tube 44 can be easily wiped down, eliminating the difficulties of cleaning the inside of a long, narrow tube. Collet 42 can also be wiped down on the outer and inner surfaces, which are again, easier to reach due to the short length of the inner surface. Although a half-tube is described in this embodiment, it is contemplated that other open configurations, including open rectangular or square shapes, flattened rods, or structures of less-than-half or more-than-half could be used to form body 6.

To facilitate cleaning, surfaces of body 6 may be relatively smooth and include fewer grooves, crevices, gaps, or areas where biofilms and bacteria could collect. The shape and finish of body 6 may facilitate wiping down after use. Additionally, body 6 may include an antibacterial coating, powder coating, or polished finish or coating to facilitate cleaning or inhibit the build-up of bacteria or biofilms.

Figure 22C:
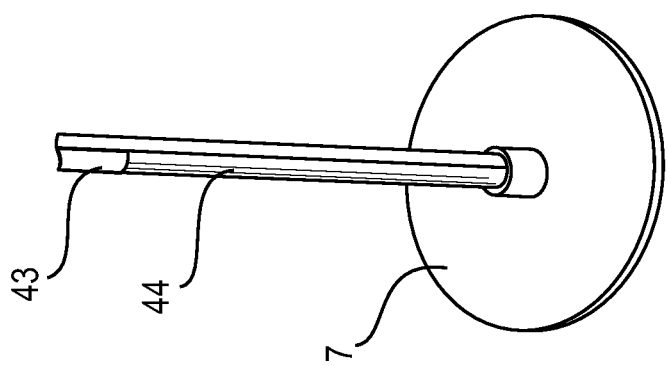
FIGS. 22A-22C depict lower portions of exemplary stands, according to embodiments of the present disclosure.
Figure 22B:
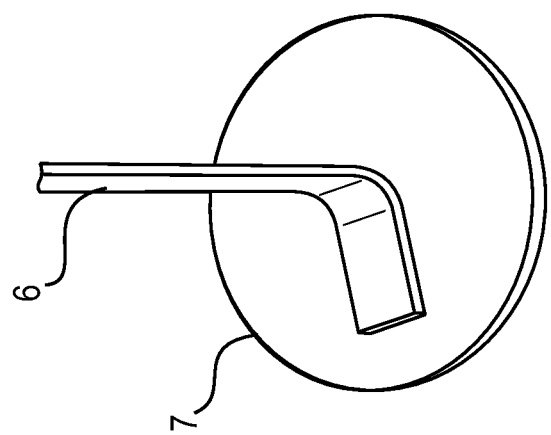
Figure 22A:
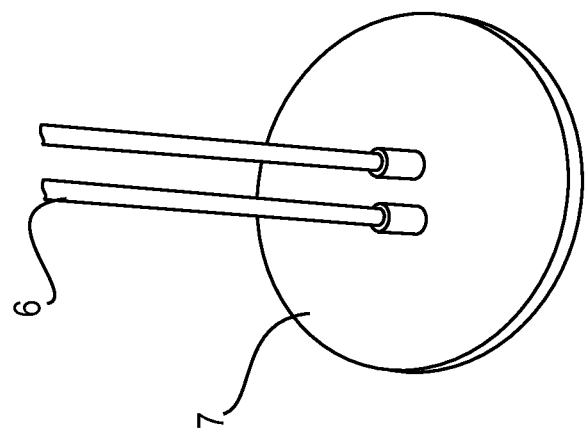

Body 6 may be formed of light-weight but sturdy materials so as to facilitate transport of stand 10 between procedures or during procedures. Exemplary materials include metals (e.g., aluminum, stainless steel, titanium, or magnesium, or combinations or alloys thereof) and/or a sturdy plastic or other suitable material. Body 6 may be attached to base 7 in any suitable manner, for example via welding (as is shown in FIGS. 22A-22C), or by a snap-fit, friction-fit, screw-fit, buckle, bayonet, latch, lock, or otherwise secure connection. Alternatively, body 6 may be integrated with base 7 as one piece.

Like body 6, base 7 preferably has a streamlined design so that stand 10 interferes as little as possible with the movement of medical staff and/or transport. In exemplary embodiments, the footprint of base 7 may range from about 20-40 cm in length and about 20-40 cm in width. The thickness of base 7 may range from about 0.5-10 cm, or from 5 to 20 cm.

Figure 24B:
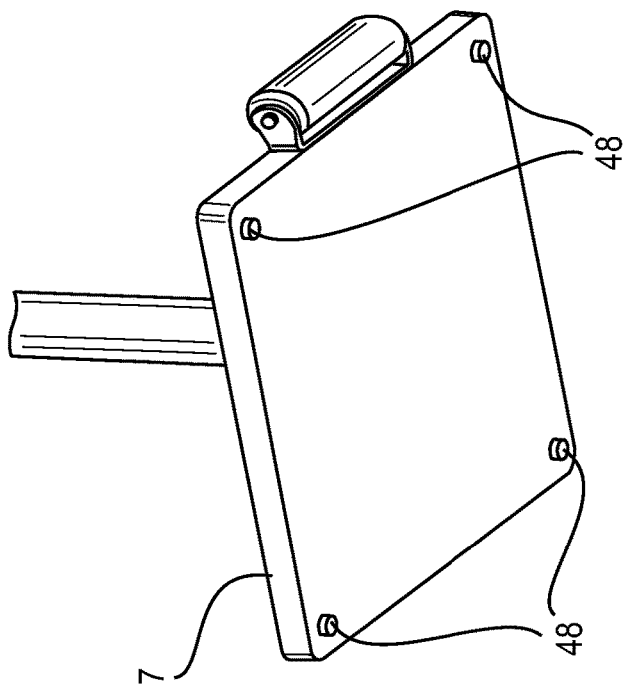
FIGS. 24A and 24B depict upper and lower perspective views of an exemplary base, according to a further embodiment of the present disclosure.
Figure 24A:
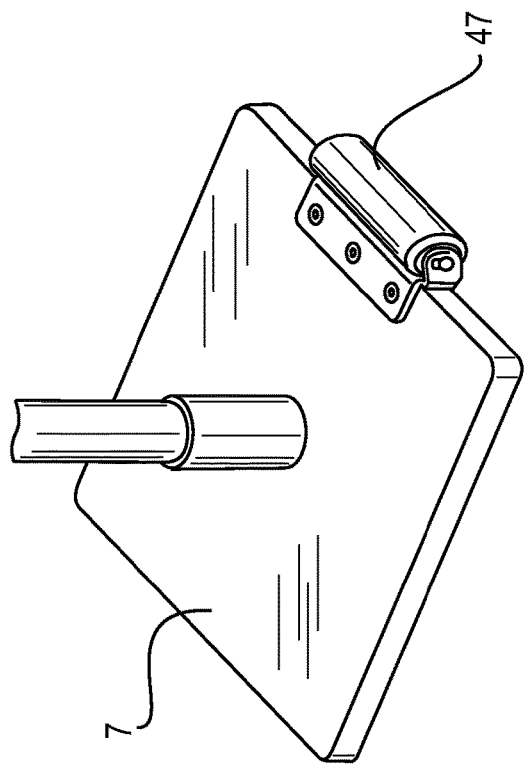

Base 7 is shaped and weighted to accommodate and support the weight and moments of endoscope 2, including the umbilical cord and the insertion tube, when attached to stand 10. Stand 10 should be stable as the physician interacts with endoscope 2 and applies forces to stand 10 and/or endoscope 2 during use. The embodiments of FIGS. 23A-23L show exemplary footprints of base 7 that are designed to increase stability of stand 10 while also not getting in the way of the physician. Triangular permutations, like those shown, may offer more stability, although it is envisioned that other shapes and/or permutations could be used. For example, a square-shaped base 7 is shown in FIGS. 24A and 24B.

As shown in FIGS. 23B, 23D, 23F, 23H, 23J, and 23L, in some embodiments, base 7 may not lay flat on the ground. Instead, the bottom of base 7 may be angled, for example, to resist tipping and to accommodate movement of endoscope 2 or the insertion tube or umbilical cord. For example, the front and/or back of base 7 may be angled downwards. In other embodiments, base 7 may lay flat on the ground. In the exemplary embodiment of FIG. 24B, base 7 may include 1 or more legs 48 protruding from the bottom surface of base 7. Legs 48 may provide additional stability and/or may inhibit sliding of base 7 during use. To this end, base 7 may also include a coating or non-skid surface to inhibit sliding, twisting, or other movement.

The weight of base 7 in some exemplary embodiments may range from about 3 kg-15 kg, and in some embodiments, from about 6 kg-12 kg. This weight may be evenly distributed around base 7 or may be centered at certain locations to promote stability.

As is shown in the exemplary figures, base 7 may also include one or more rollers 47 to facilitate transport of stand 10 between or during uses. Roller 47 may be fixedly coupled to base 7, or may be movably coupled to base 7, for example, to lift up off the floor when not in use. In some embodiments, roller 47 may lock when not in use to prevent stand 10 from accidentally rolling.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. An endoscope floor stand consisting of:
   a base;
   an adjustable body, including:
      at least a first elongated structure having a first end and a second end, wherein the first end is connected to the base; and
      at least a second elongated structure slideably moveable relative to the first elongated structure to adjust a height of the endoscope floor stand, wherein the second elongated structure is suspended above the base;
   a ball joint, wherein at least a portion of the ball joint is configured to removably couple to an end of the body located opposite the base; and
   a holder extending from the ball joint and dimensioned to receive an endoscope.

2. The endoscope floor stand of claim 1, wherein the ball joint is fully pre-assembled, and the pre-assembled ball joint is removably coupled to the end of the body.

3. The endoscope floor stand of claim 1, wherein the ball joint is included as part of the holder, and the ball joint and holder removably couple to the end of the body.

4. The endoscope floor stand of claim 1, wherein a ball of the ball joint is included as part of the holder.

5. The endoscope floor stand of claim 1, wherein a ball of the ball joint is included as part of the body.

6. The endoscope floor stand of claim 5, wherein the portion of the ball joint configured to removably couple to the end of the body includes a recess configured to receive the ball of the ball joint.

7. The endoscope floor stand of claim 1, wherein the end of the body located opposite the base includes a recess for receiving a ball of the ball joint.

8. The endoscope floor stand of claim 1, wherein a resistance to movement of the ball joint is adjustable.

9. The endoscope floor stand of claim 1, wherein the holder moves relative to a ball of the ball joint and independent from the ball of the ball joint.

10. The endoscope floor stand of claim 9, wherein a resistance of the holder to movement is different than a resistance of the ball to movement.

11. The endoscope floor stand of claim 1, wherein the ball joint is configured to allow the holder to move relative to the body within a first range of 0-180 degrees in a first plane, within a second range of 0-180 degrees in a second plane, and within a third range of 0-360 degrees in a third plane.

12. The endoscope floor stand of claim 1, wherein the ball joint is configured to allow the holder to rotate relative to the body.

13. The endoscope floor stand of claim 1, wherein the body does not include telescoping portions.

14. The endoscope floor stand of claim 1, wherein the body includes at least one telescoping portion.

15. The endoscope floor stand of claim 1, wherein the body is formed of an inner tube slideably disposed within an outer tube, wherein the outer tube does not wrap completely around a perimeter of the inner tube so that a portion of the inner tube is exposed when disposed within the outer tube.

16. The endoscope floor stand of claim 1, wherein the body further includes a third elongated structure having a first end and a second end, wherein the first end of the third elongated structure is connected to the base, and wherein the second elongated structure is suspended above the base between the first elongated structure and the third elongated structure.

17. An endoscope floor stand consisting of:
a weighted base;
a body having an adjustable height, the body including:
at least a first elongated structure extending up from the base and having a first end coupled to the base and a second end;
an adjustment mechanism located at a region of the second end of the first elongated structure; and
at least a second elongated structure moveably coupled to the adjustment mechanism, wherein the adjustment mechanism and the second elongated structure cooperatively make the height of the body adjustable;
a ball joint, wherein at least a portion of the ball joint is configured to removably couple to the body at a region opposite the base; and
a holder coupled to the ball joint and configured to receive an endoscope, wherein the ball joint is configured to allow the holder to move relative to the body in at least three degrees of freedom.

18. The endoscope floor stand of claim 17, wherein the holder is rotatable.

19. The endoscope floor stand of claim 17, wherein a ball of the ball joint is located on an end of the body opposite the base.

20. The endoscope floor stand of claim 19, wherein the ball joint is formed of the ball and an adapter, wherein the adapter has a recess configured to receive at least a portion of the ball, wherein the adapter is removably coupled to the ball, and wherein the adapter includes a fastening mechanism configured to tighten the adapter around the ball.

21. The endoscope floor stand of claim 20, wherein the adapter is included as part of the holder.

22. The endoscope floor stand of claim 17, wherein the holder is configured to rotate relative to the ball joint.

23. The endoscope floor stand of claim 22, wherein a resistance of the holder to movement is different than a resistance of the ball joint to movement.

24. The endoscope floor stand of claim 17, wherein the ball joint includes a ball and at least one of a locking nut or a locking adapter.

25. The endoscope floor stand of claim 24, wherein the body includes a recess located on an end of the body opposite the base, and wherein the recess is configured to receive the ball.

26. A device for coupling to a body of an endoscope stand for holding an endoscope during use, the device consisting of:
an adapter having a recess configured to receive a rounded portion of the body of the endoscope stand to cooperatively form a ball joint, wherein the adapter is configured to removably couple the device to the rounded portion of the endoscope stand;
a fastening mechanism configured to compress the adapter to couple the device to the body of the endoscope stand; and
a holder coupled to the adapter and configured to receive an endoscope, wherein the holder is moveable around the rounded portion of the endoscope stand in at least three degrees of freedom when coupled to the body of the endoscope stand.

27. The device of claim 26, wherein the holder is rotatably coupled to the adapter.

28. The device of claim 26, wherein the holder is removably coupled to the adapter.

29. The device of claim 26, wherein the device further includes at least one of a locking nut, a locking adapter, a buckle, or a screw mechanism for tightening the adapter.

* * * * *